(12) United States Patent
Eslava et al.

(10) Patent No.: US 11,853,123 B2
(45) Date of Patent: Dec. 26, 2023

(54) DISPLAY MONITORS AND MONITOR MOUNT

(71) Applicant: DRÄGERWERK AG & CO. KGAA, Lubeck (DE)

(72) Inventors: Juan P. Eslava, Groton, MA (US); Peter Lund, Nashua, NH (US)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 0 days.

(21) Appl. No.: 17/873,851

(22) Filed: Jul. 26, 2022

(65) Prior Publication Data

US 2022/0365559 A1 Nov. 17, 2022

Related U.S. Application Data

(63) Continuation of application No. 16/707,577, filed on Dec. 9, 2019, now Pat. No. 11,449,101, which is a continuation of application No. 16/314,297, filed as application No. PCT/US2017/066128 on Dec. 13, 2017, now Pat. No. 10,539,977.

(60) Provisional application No. 62/439,427, filed on Dec. 27, 2016.

(51) Int. Cl.
| | |
|---|---|
| *G06F 1/16* | (2006.01) |
| *H05K 5/00* | (2006.01) |
| *H05K 7/00* | (2006.01) |
| *A61B 5/0205* | (2006.01) |
| *A61B 5/00* | (2006.01) |

(52) U.S. Cl.
CPC ............ *G06F 1/1632* (2013.01); *A61B 5/002* (2013.01); *A61B 5/0205* (2013.01); *A61B 5/7275* (2013.01); *A61B 5/742* (2013.01); *A61B 5/7445* (2013.01); *G06F 1/1654* (2013.01); *A61B 2560/0456* (2013.01)

(58) Field of Classification Search
CPC ..... G06F 1/1632; G06F 1/1654; A61B 5/002; A61B 5/0205; A61B 5/7275; A61B 5/742; A61B 5/7445
See application file for complete search history.

(56) References Cited

U.S. PATENT DOCUMENTS

| | | | |
|---|---|---|---|
| 9,161,696 B2 * | 10/2015 | Al-Ali | ....................... A61B 5/74 |
| 2010/0207903 A1 * | 8/2010 | Kim | .................... H04M 1/0254 |
| | | | 345/1.3 |
| 2010/0261979 A1 * | 10/2010 | Kiani | ................... A61B 5/0002 |
| | | | 600/301 |

(Continued)

*Primary Examiner* — Anthony M Haughton
(74) *Attorney, Agent, or Firm* — Nolte Lackenbach Siegel

(57) ABSTRACT

A system includes a monitor mount and first and second monitors. The monitor mount includes a first coupling, a second coupling, and a first power bus. The first monitor includes a first electronic visual display and has a size and shape configured to be detachably secured to the monitor mount by the first coupling. The first monitor can optionally be powered by the first power bus when secured to the monitor mount. The second monitor includes a second electronic visual display and a third coupling. The second monitor has a size and shape configured to: (i) be detachably secured to the monitor mount by the second coupling, (ii) detachably secure the first monitor by the third coupling, and (iii) surround at least a portion of the first electronic visual display when the first monitor is secured to the second monitor.

23 Claims, 22 Drawing Sheets

(56) References Cited

U.S. PATENT DOCUMENTS

2011/0054268 A1* 3/2011 Fidacaro .................. G06F 1/16
　　　　　　　　　　　　　　　　　　　　　361/679.01
2016/0094691 A1* 3/2016 Okuley ................ G06F 1/1632
　　　　　　　　　　　　　　　　　　　　　455/575.1

* cited by examiner

DISPLAY MONITORS AND MONITOR MOUNT

PRIORITY CLAIM

The present application is a continuation and claims priority to U.S. application Ser. No. 16/707,577 filed Dec. 9, 2019; U.S. application Ser. No. 16/314,297, filed Dec. 28, 2018; International PCT/US2017/066128 filed Dec. 13, 2017; and U.S. Provisional Application Ser. No. 62/439,427, filed Dec. 27, 2016, the contents of all of which are incorporated by reference herein in their entirety.

TECHNICAL FIELD

The subject matter described herein relates to monitors having electronic visual displays and monitor mounts for use with such monitors.

BACKGROUND

Monitors that include electronic visual displays are utilized in a large number of applications within a wide variety of industries including, for example, healthcare, military, and oil and gas. Many of the applications within such industries require such monitors to, at times, be portable, and, at other times, be stationary. When not used in transport of a patient or when a patient is ambulatory, monitors at times can be sometimes connected to a monitor mount. Such monitor mounts can provide a variety of functions including physical support, a power source, and a conduit to one or more computer networks.

One type of a monitor is a patient monitor which is used by health care facilities to monitor and display information about a patient such as vital signs, status of connected devices (e.g., physiological sensors, etc.), and the like. Patient monitors typically are portable devices that travel with the patient in order to provide continuous monitoring during care. When a patient arrives at a hospital room or other treatment location, the patient monitor is often plugged into or otherwise connected to a patient monitor mount. Patient monitor mounts provide a physical interface for the patient monitor and are generally fixed to the treatment location. Patient monitor mounts also provide electrical connection to other devices or infrastructure, such as power to recharge patient monitor batteries, network connectivity to other medical devices or hospital computer systems, and the like.

SUMMARY

In one aspect, a system includes a monitor mount and first and second monitors. The monitor mount includes a first coupling, a second coupling, and a first power bus. The first monitor includes a first electronic visual display and has a size and shape configured to be detachably secured to the monitor mount by the first coupling. The first monitor can optionally be powered by the first power bus when secured to the monitor mount. The second monitor includes a second electronic visual display and a third coupling. The second monitor has a size and shape configured to: (i) be detachably secured to the monitor mount by the second coupling, (ii) detachably secure the first monitor by the third coupling, (iii) surround at least a portion of the first electronic visual display when the first monitor is secured to the second monitor.

The second monitor can be powered by the first power bus when the first monitor is secured to the second monitor and both of the first monitor and the second monitor are secured to the monitor mount.

The first monitor can also include a second power bus and the second monitor is powered by the second power bus when the first monitor is secured to the second monitor. The second monitor, in some variations, is operable solely via the second power bus. In other variations, the second monitor is operable via either of the first power bus and the second power bus.

The first monitor can include a self-contained power source that allows the first monitor to be operated independent of the monitor mount.

The first monitor can include a sensor interface configured to receive data generated by at least one physiological sensor monitoring a physiological parameter of a patient. The at least one physiological sensor can include a wired connection to the sensor interface. The at least one physiological sensor can additionally or alternatively include a wireless connection to the sensor interface.

The second monitor can be configured to be first coupled to the second coupling and the first monitor can be configured to be subsequently coupled to the third coupling and the first coupling.

The first monitor can be configured to be coupled to and power the second monitor by the second power bus when neither of the first monitor and the second monitor are secured to the monitor mount.

The first coupling, the second coupling, and the third coupling can take various forms including a mechanical coupling, an electro-mechanical coupling, and/or a magnetic coupling.

The monitor mount can further include a first communications interface coupled to at least one computing network. With this variation, the first monitor can include a second communications interface which transmits and receives data over the computing network via the first communications interface when the first monitor is secured to the monitor mount.

The second monitor can include a third communications interface for receiving data from the second communications interface of the first monitor and for visualizing at least a portion of such received data on the second electronic visual display.

The first monitor can be configured to be detachably secured to and removed from a forward face of the monitor mount. In addition or the alternative, the first monitor can be configured to be transversely inserted into and removed from the monitor mount.

The first monitor can be configured to be transversely inserted into and removed from the second monitor.

In an interrelated aspect, a system for use with a monitor mount having a first coupling, a second coupling, and a first power bus can include a first monitor and a second monitor both as described herein.

In an further interrelated system, a monitor mount can include a first coupling, a second coupling, and a first power bus. Such a monitor mount is configured to detachably secure a first monitor and a second monitor both as described herein.

Non-transitory computer program products (i.e., physically embodied computer program products) are also described that store instructions, which when executed by one or more data processors of one or more computing systems, cause at least one data processor to perform operations herein. Similarly, computer systems are also described that can include one or more data processors and memory coupled to the one or more data processors. The memory can temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g., the Internet, a wireless wide area network, a local area network, a wide area network, a wired network, or the like), via a direct connection (e.g., electrical connection) between one or more of the multiple computing systems, etc.

The subject matter described herein provides many technical advantages. For example, the current subject matter enables the mounting of two monitors having different sizes, shapes, and functionality on a single monitor mount.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

Like reference symbols in the various drawings indicate like elements.

DETAILED DESCRIPTION

The subject matter described herein is directed to systems and apparatuses directed to monitors (e.g. display monitors having visual electronic displays) and monitor mounts providing physical support and, in some cases, power and access to a communications/computer network. Use of such systems and apparatuses can, for example, occur in a medical environment such as a hospital or doctor's office. When a patient undergoes initial patient monitoring in such an environment, a minimum set of sensors can be connected to a patient to collect various types of patient information as described in detail herein. As a patient is moved from one area of care within the medical environment to another area of care, the patient monitor can travel with the patient. In some situations, the patient monitor can be mounted to a monitor mount to provide for stationary observation of the patient information on a visual electronic display. During the course of patient monitoring, the number of sensors can also increase due to increased testing and/or monitoring of the patient. In such a scenario, a patient monitor initially monitoring the patient can be docked into monitor mount having a second, larger monitor in order to expand the number of sensors available for patient monitoring and/or increase the number of patient parameters on a single visual electronic display by docking the patient monitoring device within a larger patient monitor. The initial patient monitor can either remain within the larger patient monitor or be removed from the larger patient monitor.

Figure 1:
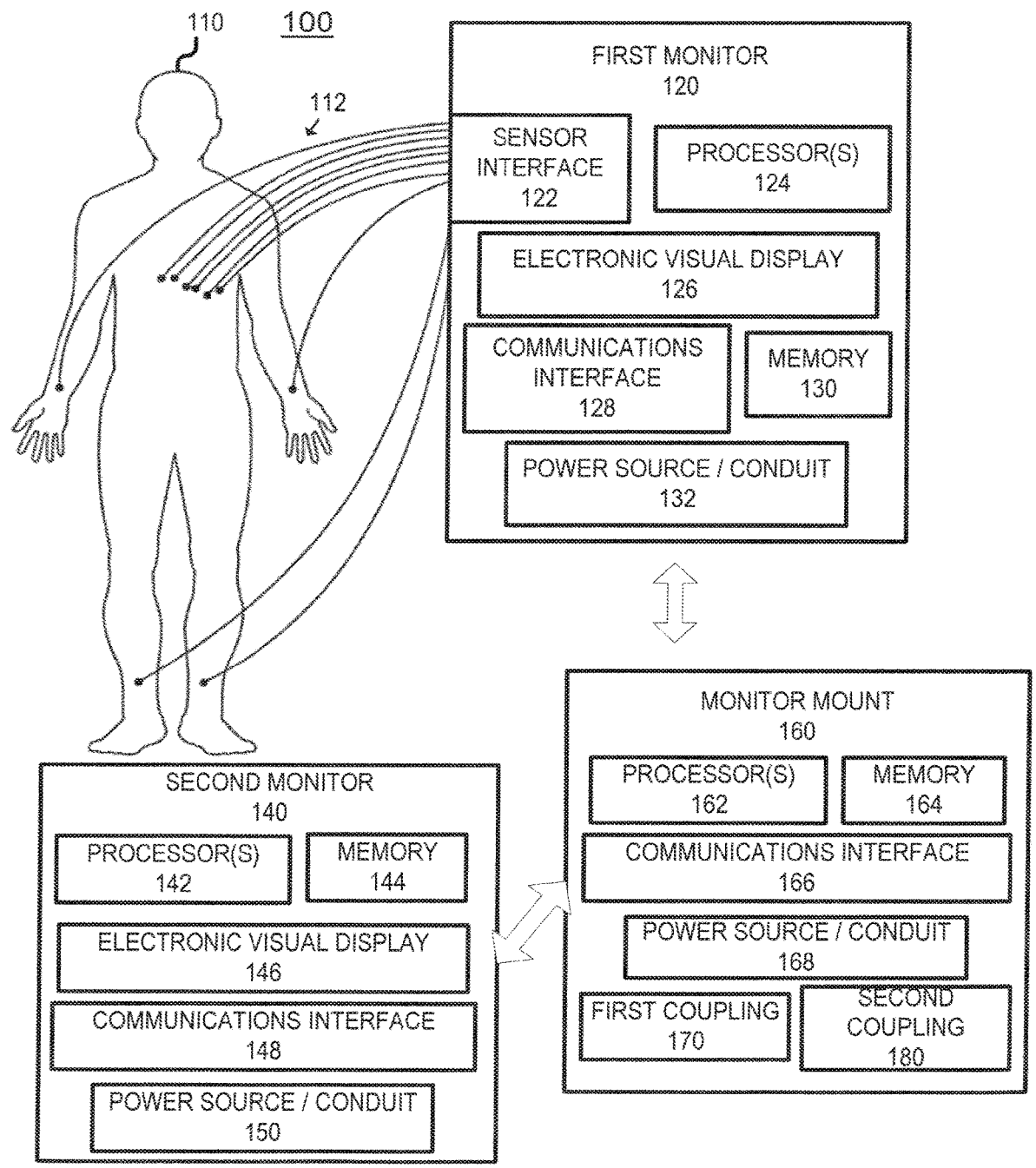
FIG. 1 is a logic diagram illustrating a first monitor, a second monitor and a monitor mount.
Figure 21:
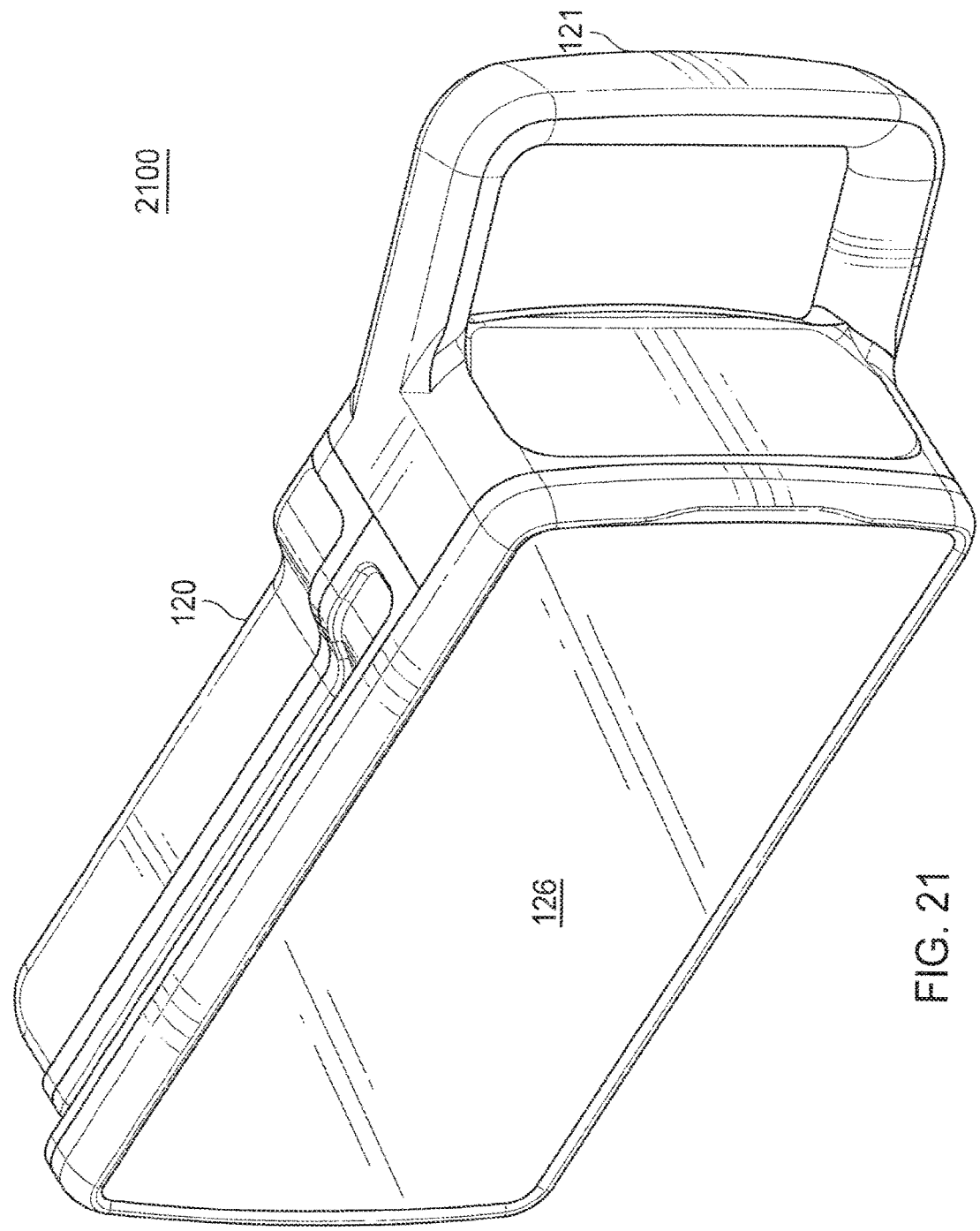
FIG. 21 is a front perspective view of another alternative first monitor.
Figure 22:
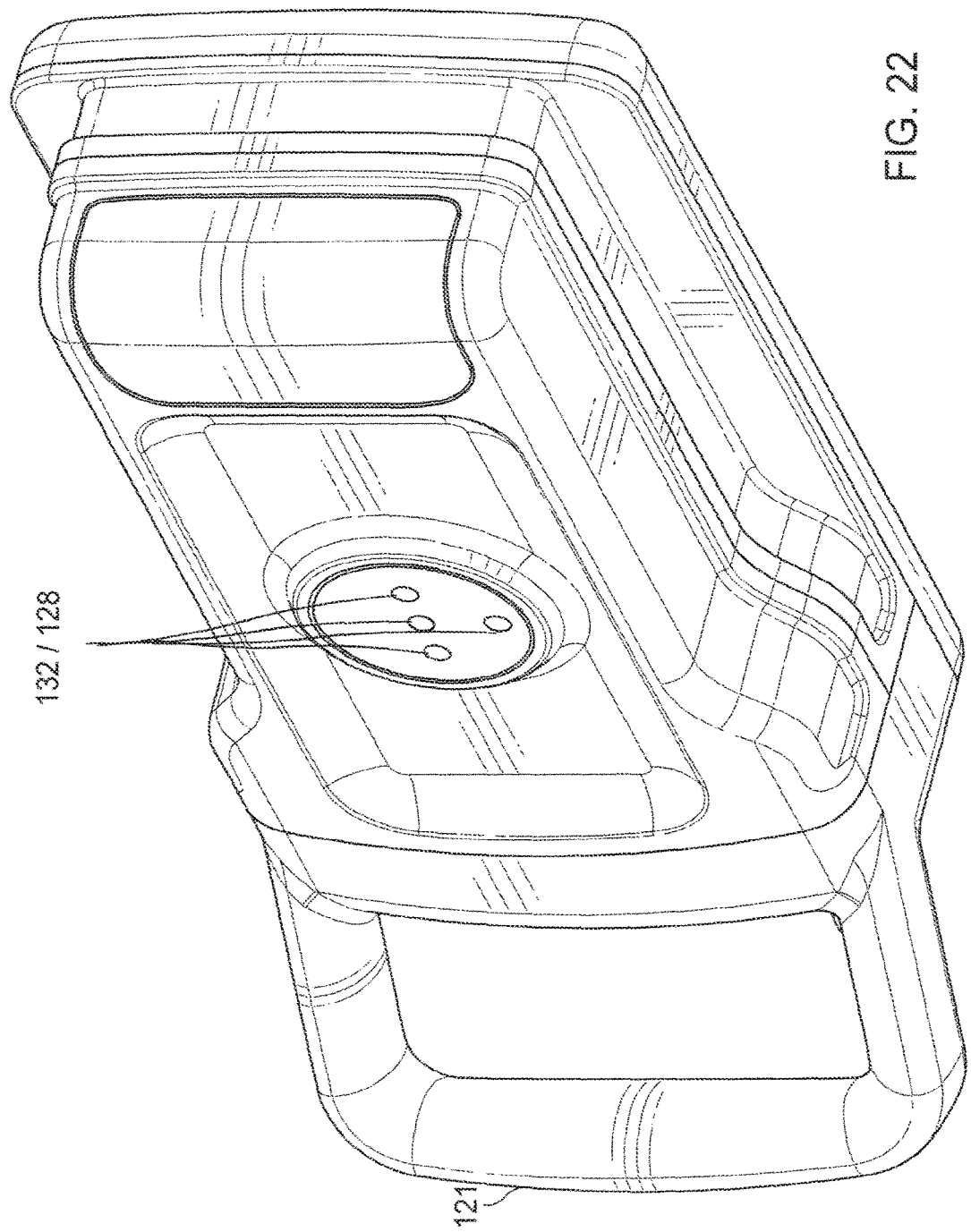
FIG. 22 is a back perspective view of another alternative first monitor of FIG. 21.

FIG. 1 is a logical diagram 100 of a first monitor 120, a second monitor 140, and a monitor mount 160 which can detachably secure (or otherwise physically interface) with both of the first monitor 120 and the second monitor 140. FIGS. 2-9 are diagrams 200-900 providing various views of an example implementation of the first monitor 120, the second monitor 140, and the monitor mount 160. FIGS. 10-20 are diagrams 1000-2000 providing various views of another example implementation of the first monitor 120, the second monitor 140, and the monitor mount 160. FIGS. 21-22 are diagrams 2100-2200 providing various views of yet another example implementation of the first monitor 120.

As will be described in further detail below, the first monitor 120 has a shape and size which differs from that of the second monitor 140. Notwithstanding, both of the first and second monitors 120, 140 are able to be concurrently secured to the monitor mount 160. In addition, while certain configurations are illustrated with regard to the monitor mount 160 and the first and second monitors 120, 140, it will be appreciated that these illustrations in FIGS. 2-8 are examples and not limiting in nature (unless otherwise specified).

The first monitor 120 can, for example, be a patient monitor that is used to monitor various physiological parameters for a patient 110. With such a variation, the first monitor 120 can include a sensor interface 122 that can be used to connect via wired and/or wireless interfaces to one or more physiological sensors and/or medical devices 112 (e.g., ECG electrodes, $SPO_2$ sensor, blood pressure cuffs, apnea detection sensors, respirators, etc.) associated with the patient 110. The first monitor 120 can include one or more processors 124 (e.g., programmable data processors, etc.) which can execute various instructions stored in memory 130 of the first monitor 120. Various data and graphical user interfaces can be conveyed to a user via an electronic visual display 126. This information can, for example, relate to the measured physiological parameters of the patient 110 and the like (e.g., blood pressure, heart related information, pulse oximetry, respiration information, etc.). Other types of information can also be conveyed by the electronic visual display 126. In some variations, the electronic visual display 126 includes a touch screen interface.

The first monitor 120 can additionally include a communications interface 128 which allows the first monitor 120 directly or indirectly (via, for example, the monitor mount 160) to access one or more computing networks. The communications interface 128 can include, various network cards/interfaces to enable wired and wireless communications with such computing networks. The communications interface 128 can also enable direct (i.e., device-to-device, etc.) communications (i.e., messaging, signal exchange, etc.) such as from the monitor mount 160 to the first monitor 120.

The first monitor 120 can optionally also include a power source and/or conduit 132 that can be used to power the various components of the first monitor 120. The power source/conduit 132 can include a self-contained power source such as a battery pack and/or it can include an interface to be powered through an electrical outlet (either directly or by way of the monitor mount 160).

The second monitor 140 can include one or more processors 142 (e.g., programmable data processors, etc.) which can execute various instructions stored in memory 144 of the second monitor 140. Various data and graphical user interfaces can be conveyed to a user via an electronic visual display 146. This information can, for example, relate to the measured physiological parameters of the patient 110 and the like (e.g., blood pressure, heart related information, pulse oximetry, respiration information, etc.) as received from the first monitor 120. Other types of information can also be conveyed by the electronic visual display 146. In some variations, the electronic visual display 146 includes a touch screen interface.

The second monitor 140 can additionally include a communications interface 148 which allows the second monitor 140 directly or indirectly (via, for example, the first monitor 120 and/or the monitor mount 160) to access one or more computing networks. The communications interface 148 can include, various network cards/interfaces to enable wired and wireless communications with such computing networks. The communications interface 148 can also enable direct (i.e., device-to-device, etc.) communications (i.e., messaging, signal exchange, etc.) such as from the monitor mount 160 to the second monitor 140 and the first monitor 120 to the second monitor 140.

The second monitor 140 can optionally also include a power source and/or conduit 150 that can be used to power the various components of the first monitor 120. The power source/conduit 150 can include a self-contained power source such as a battery pack and/or it can include an interface to be powered through an electrical outlet (either directly or by way of the first monitor 120 and/or the monitor mount 160). In some variations, the second monitor 140 can only be powered and render information when secured or otherwise connected to one or more of the first monitor 120 and the monitor mount 160.

The monitor mount 160 can include one or more processors 162 (e.g., programmable data processors, etc.) which can execute various instructions stored in memory 164 of the monitor mount 160. The monitor mount 160 can additionally include a communications interface 166 which allows the monitor mount 160 directly or indirectly to access one or more computing networks. The communications interface 166 can include, various network cards/interfaces to enable wired and wireless communications with such computing networks. The communications interface 166 can also enable direct (i.e., device-to-device, etc.) communications (i.e., messaging, signal exchange, etc.) such as with the first monitor 120 and/or the second monitor 140.

The monitor mount 160 can optionally also include a power source and/or conduit 168 that can be used to power the various components of the monitor mount 160 and/or the first monitor 120 and the second monitor 140 when secured to the monitor mount 160. The power source/conduit 168 can include a self-contained power source such as a battery pack and/or it can include an interface to be powered through an electrical outlet.

In some variations, the processors 162 and the memory 164 are omitted such that the monitor mount 160 provides only physical support and optionally a power source.

The monitor mount 160 has a shape and size which allows it to detachably secure both the first monitor 120 and the second monitor 140. In this regard, detachably secure means that the monitor mount 160 can secure the respective monitors 120 and 140 such that they can be removed by a user when desired.

The monitor mount 160 can include a first coupling 170 that allows the first monitor 120 to be secured at such location. The first coupling 170 can include a combination of ledges, rails, ribs, abutments, and the like to allow the first monitor 120 to be secured to the monitor mount 160. The first coupling 170 can additionally or alternatively use different securing mechanisms including magnetic and/or electromagnetic locking mechanisms which cause the first monitor 120 to selectively be secured by the monitor mount 160. In some cases, the first monitor 120 can slide into and out of the first coupling 170 from a lateral direction (i.e., from the side of the monitor mount 160) while in other variations, the first monitor 120 can be placed on and removed from the forward face of the monitor mount 160. In some implementations, the first monitor 120 can both slide into and out of the first coupling 170 from the lateral direction and be placed on and removed from the forward face of the monitor mount 160. Reference is made to view 400 of FIG. 4 which shows a portion of the first coupling 170 in which the first monitor 120 can be inserted.

The positioning of the first monitor 120, when secured to the monitor mount 160, can be such that the communications interface 128 on the first monitor 120 lines up to the communications interface 166 of the monitor mount 160 to allow, for example, a direct connection (e.g., electrical connection) In other variations, the communications interface 128 of the first monitor 120 exchanges data with the communications interface 166 of the monitor mount 160 optically (via, for example, respective optical windows on the first monitor 120 and the monitor mount 160).

The positioning of the first monitor 120 when secured to the monitor mount 160 can also align the power source/conduit 132 of the first monitor 120 to be coupled to the power source/conduit 168 of the monitor mount 160 which causes the monitor mount 160 to power the first monitor 120.

The monitor mount 160 can include a second coupling 180 that allows the second monitor 140 to be secured at such location. The second coupling 180 can include a combination of ledges, rails, ribs, abutments, and the like to allow the second monitor 140 to be secured to the monitor mount 160. The second coupling 180 can additionally or alternatively use different securing mechanisms including magnetic and/or electromagnetic locking mechanisms which cause the second monitor 140 to selectively be secured by the monitor mount 160. The positioning of the second monitor 140, when secured to the monitor mount 160, can be such that the communications interface 148 on the second monitor 140 lines up to the communications interface 166 of the monitor mount 160 to allow, for example, a direct connection (e.g., electrical connection). In other variations, the communications interface 148 of the second monitor 140 exchanges data with the communications interface 166 of the monitor mount 160 optically (via, for example, respective optical windows on the second monitor 140 and the monitor mount 160).

Second coupling 180 can enable front-to-back docking of the second monitor 140 within monitor mount 160 by providing a shelf feature extending outwardly. This feature of second coupling 180 can support and/or disperse the weight of the second monitor 140 during positioning of the second monitor 140. For example, a user attempting to position second monitor 140 within monitor mount 160 can rest second monitor 140 on second coupling 180 during the positioning while attaching a front portion of second monitor 140 to second coupling 180. A back portion of second monitor 140 such as the communications interface 140 can follow once the front portion of the second monitor 140 has been secured.

The positioning of the second monitor 140 when secured to the monitor mount 160 can also align the power source/conduit 150 of the second monitor 140 to be coupled to the power source/conduit 168 of the monitor mount 160 which causes the monitor mount 160 to power the second monitor 140. In some variations, the positioning of the second monitor 140 when secured to the monitor mount 160 and when the first monitor 120 is also secured to the monitor mount 160 can also align the power source/conduit 150 of the second monitor 140 to be coupled to the power source/conduit 132 of the first monitor 120 (which in turn is connected to the power source/conduit 168 of the monitor mount 160) which causes the first monitor 120 to power the second monitor 140

Figure 2:
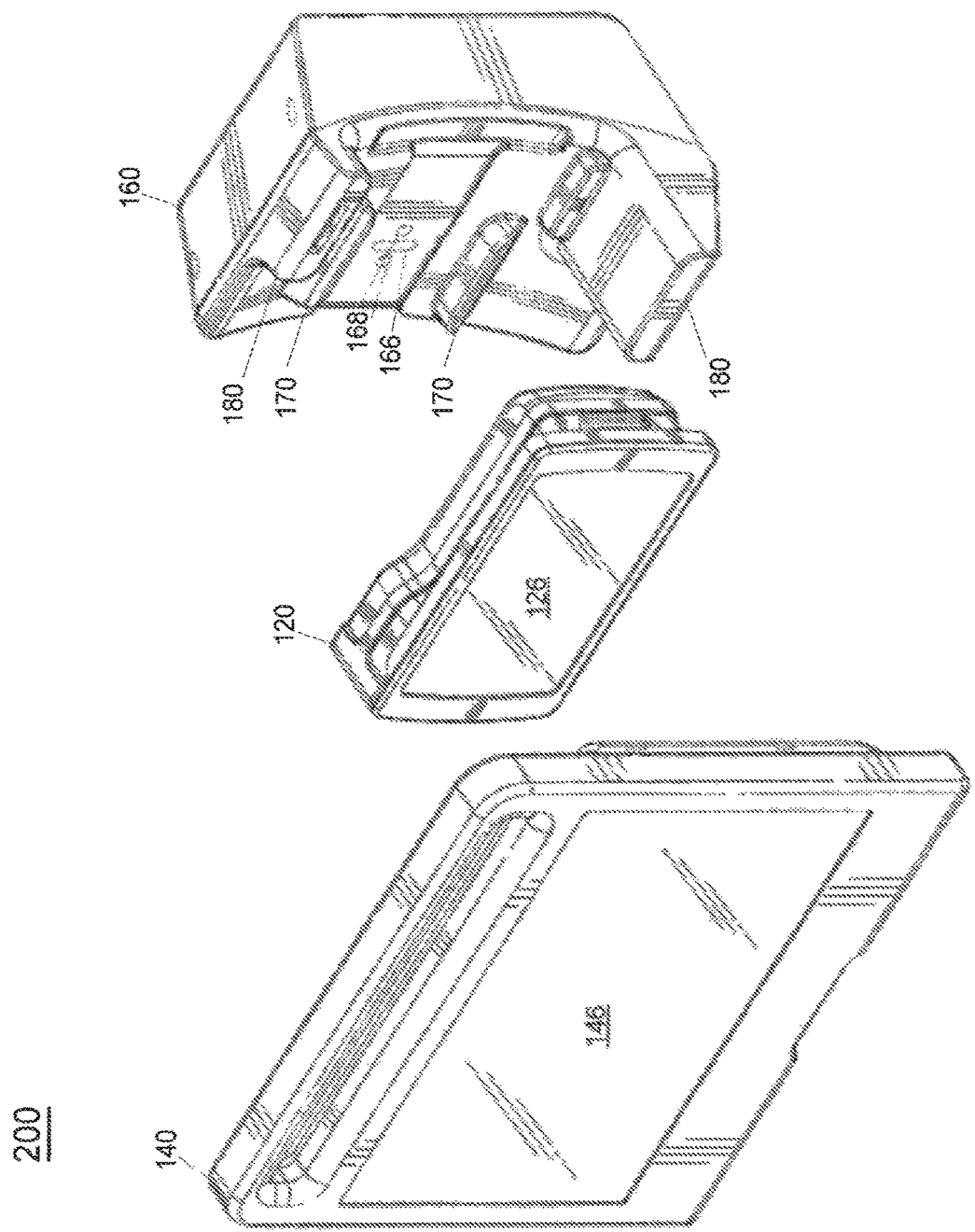
FIG. 2 is an exploded perspective view of one implementation of the first monitor, the second monitor, and the monitor mount.
Figure 3:
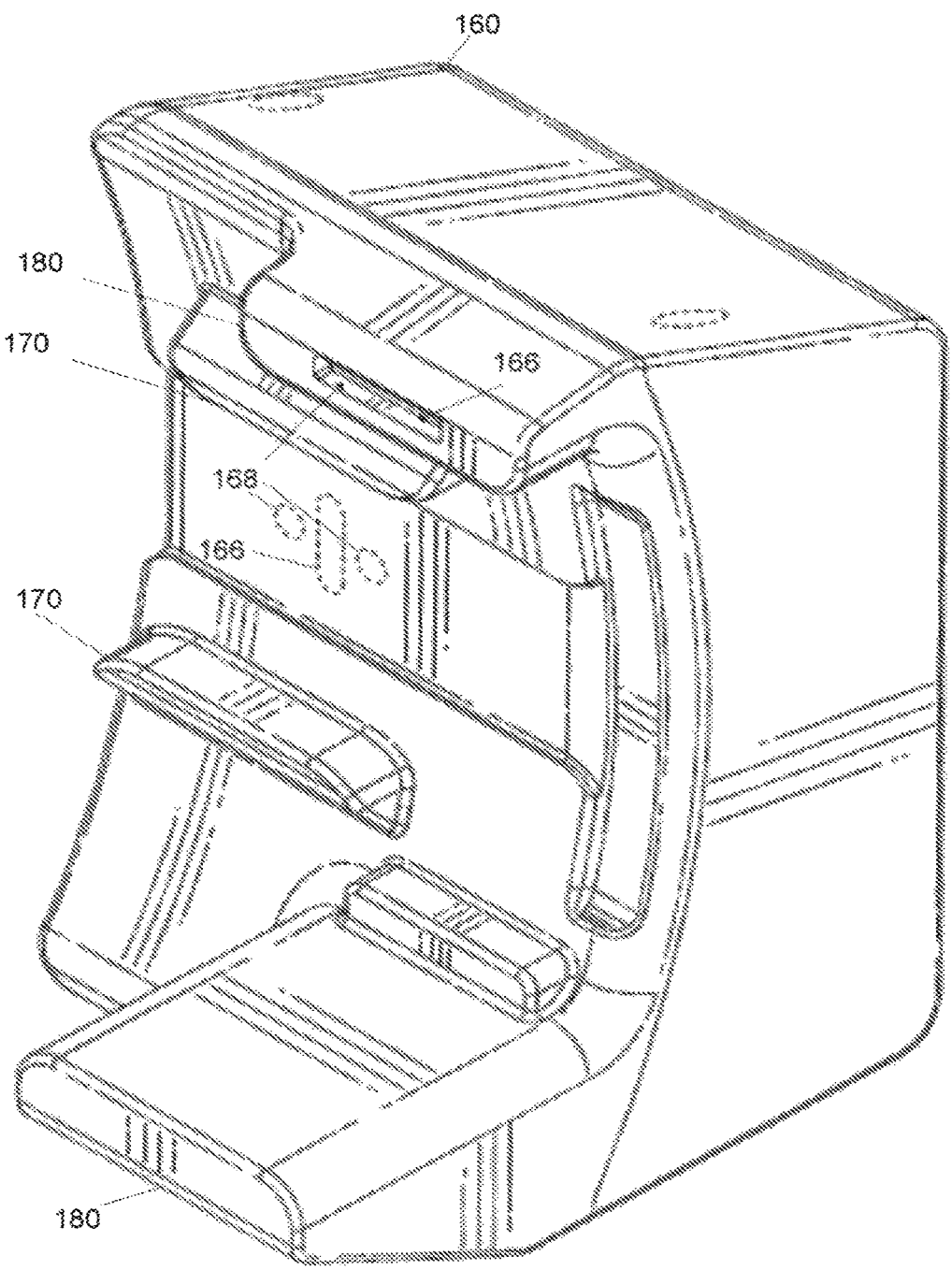
FIG. 3 is a perspective view of the monitor mount.

FIG. 2 is an exploded perspective view 200 that shows the relationship among the first monitor 120, the second monitor 140, and the monitor mount. As shown, the communications interface 166 and the power/source conduit 168 can be placed intermediate the first coupling 170 so that the first monitor 120 may interface therewith. Similarly, the communications interface 166 and the power/source conduit 168 can additionally be placed as part of the second coupling 180 (not shown) so that the second monitor 140 may interface therewith. The perspective view 300 of FIG. 3 shows additional details in this regard.

Figure 4:
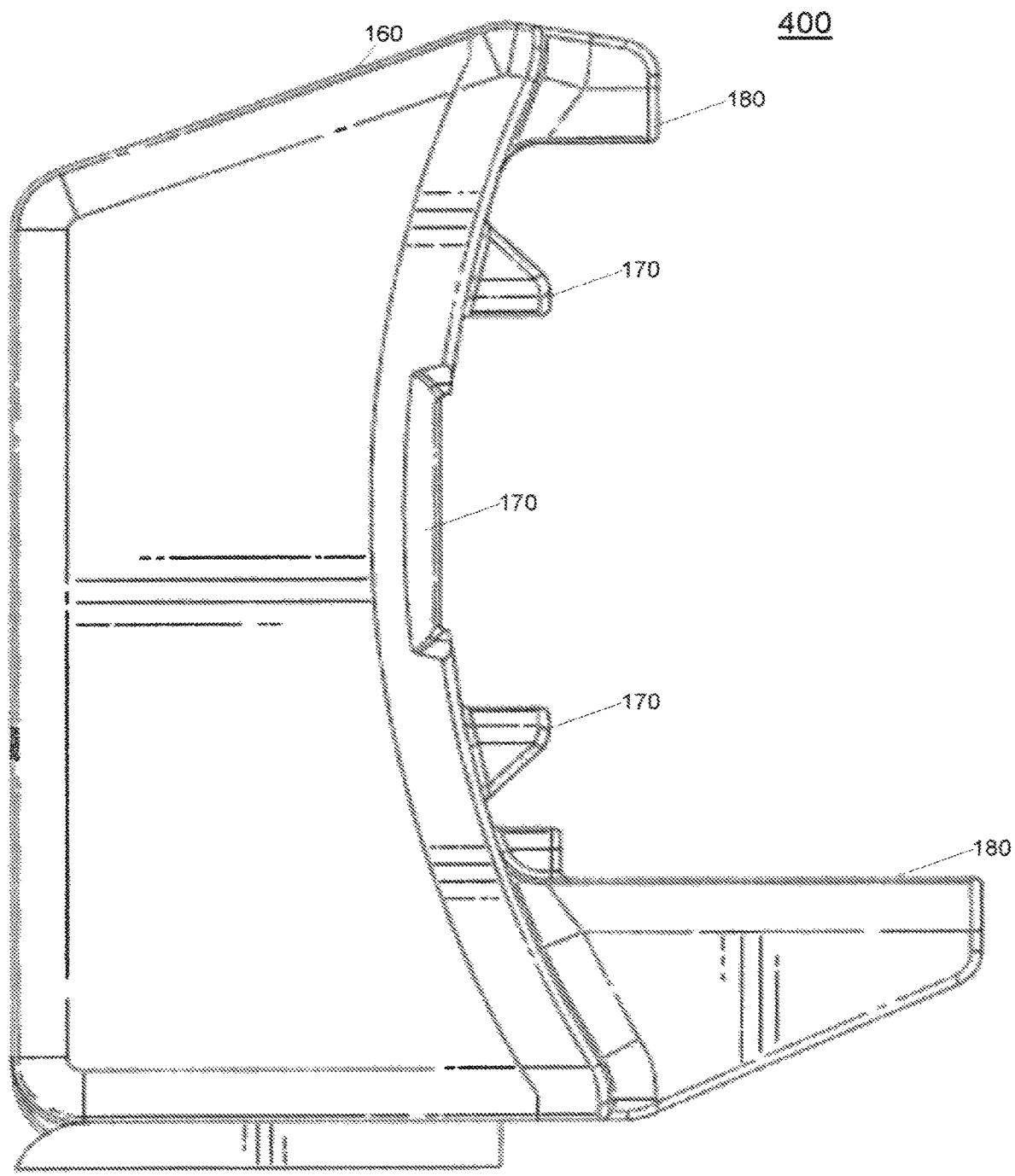
FIG. 4 is a side view of the monitor mount of FIG. 3.

FIG. 4 is a side view 400 showing various aspects of the monitor mount 160 including detail about how the first monitor 120 can be transversely inserted into the monitor mount 160 (i.e., the first monitor 120 can slide into the monitor mount 160).

Figure 5:
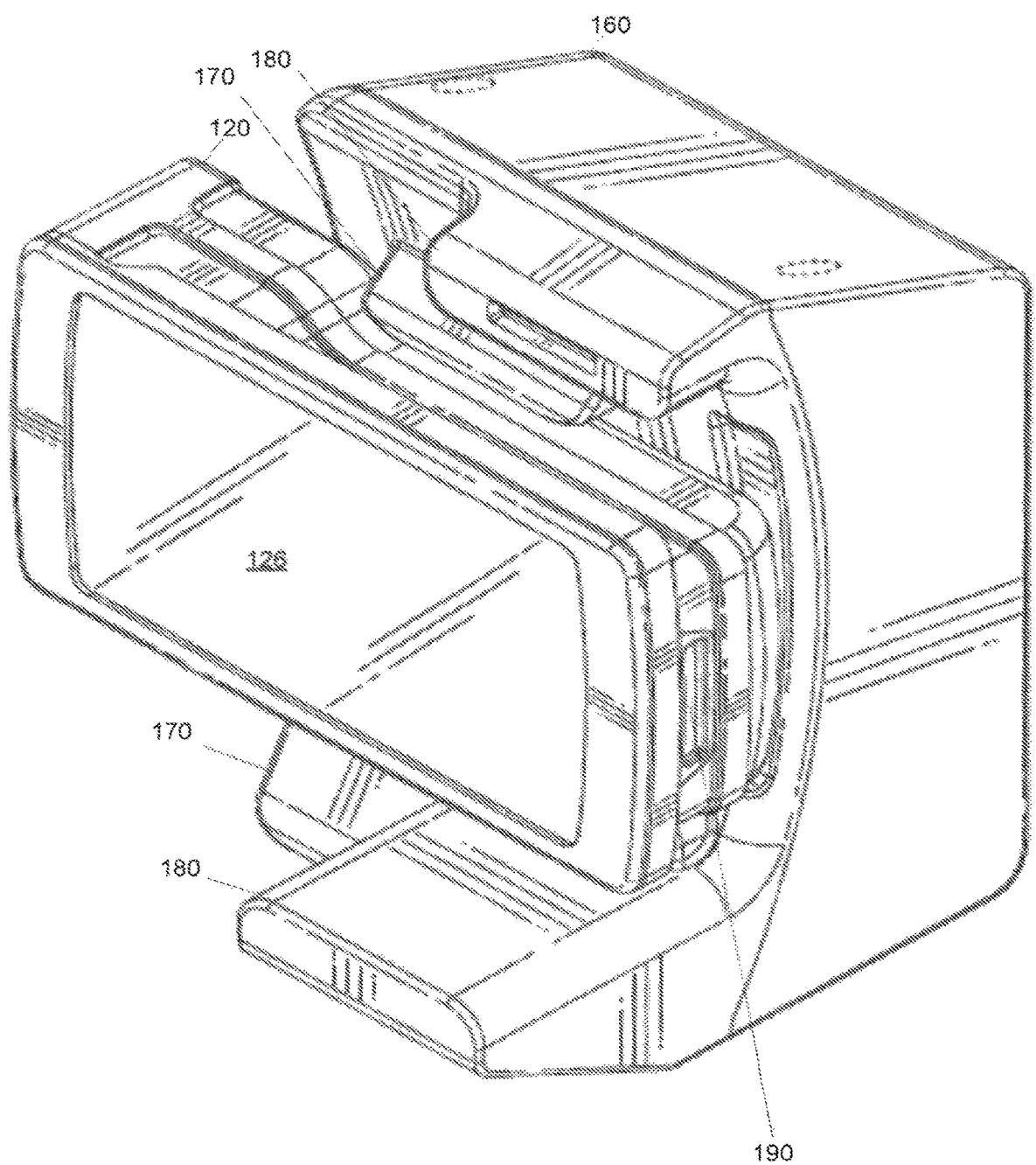
FIG. 5 is a perspective view of the monitor mount detachably securing the first monitor.

FIG. 5 is a perspective view 500 showing the first monitor 120 being detachably secured to the monitor mount 160. First monitor 120 includes a first electrical connector 190 configured to connect with a second electrical connector 195 of the second monitor 140 via a direct connection.

Figure 6:
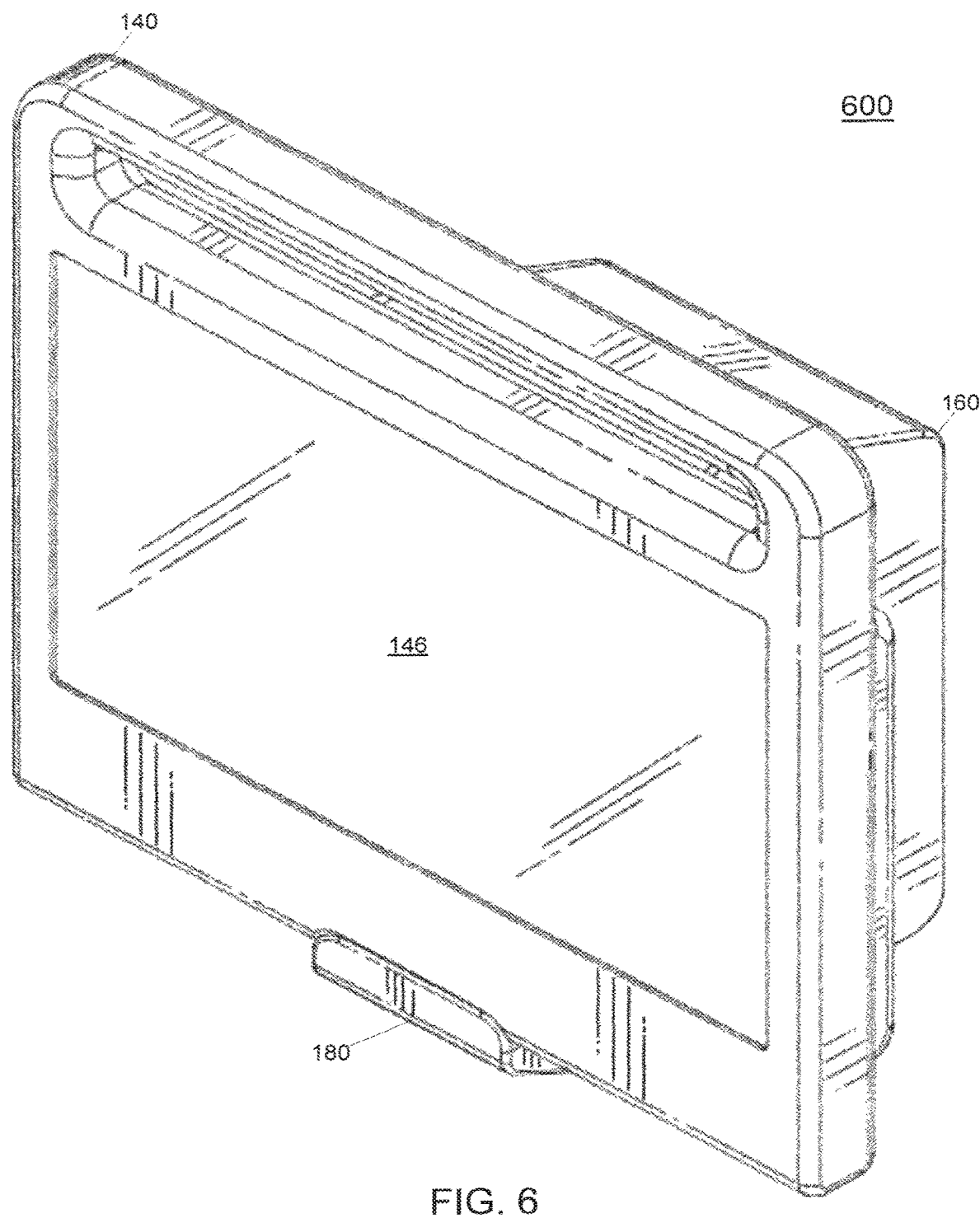
FIG. 6 is a perspective view of the monitor mount detachably securing the second monitor.
Figure 7:
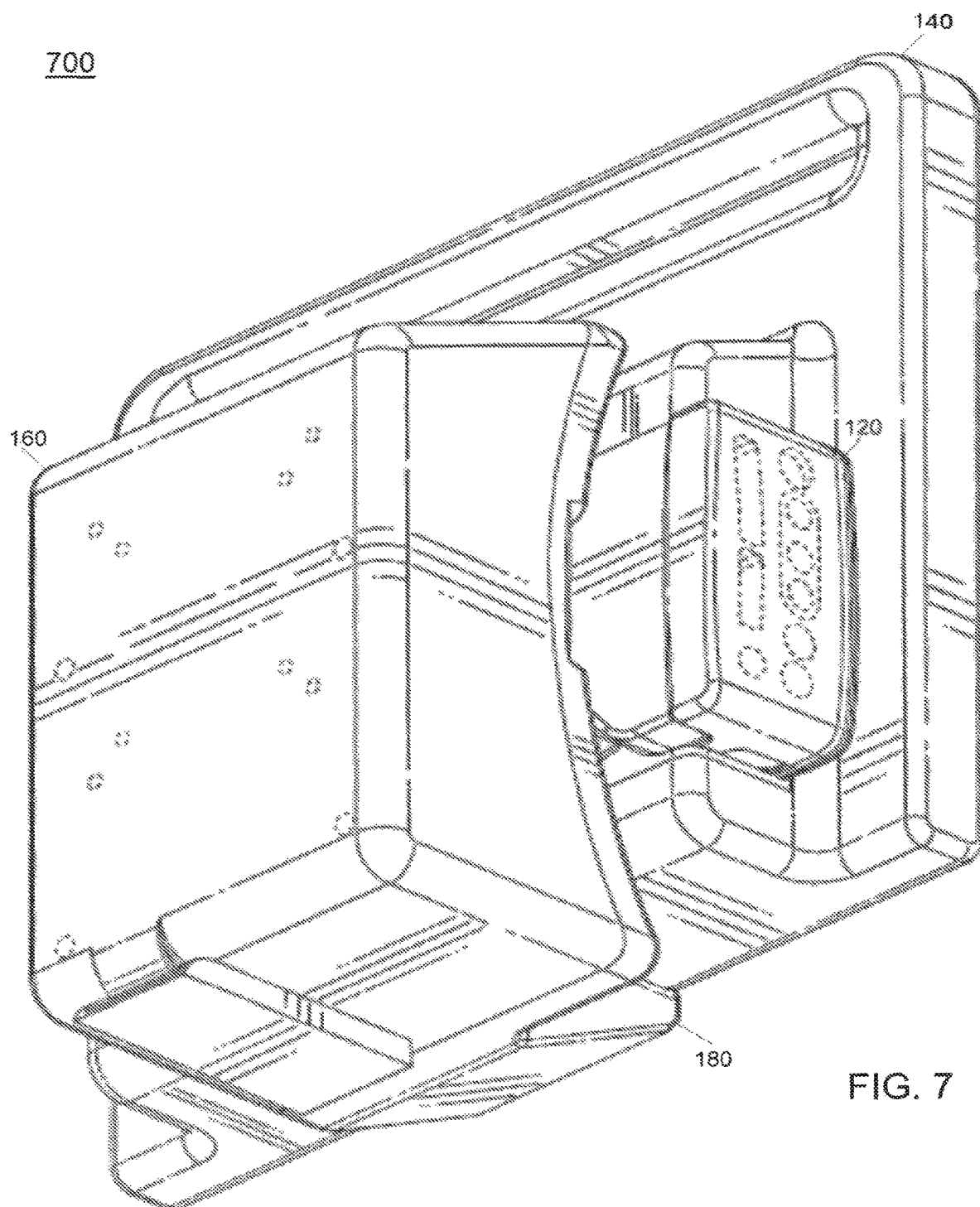
FIG. 7 is a perspective view of the monitor mount detachable securing both the first monitor and the second monitor.
Figure 8:
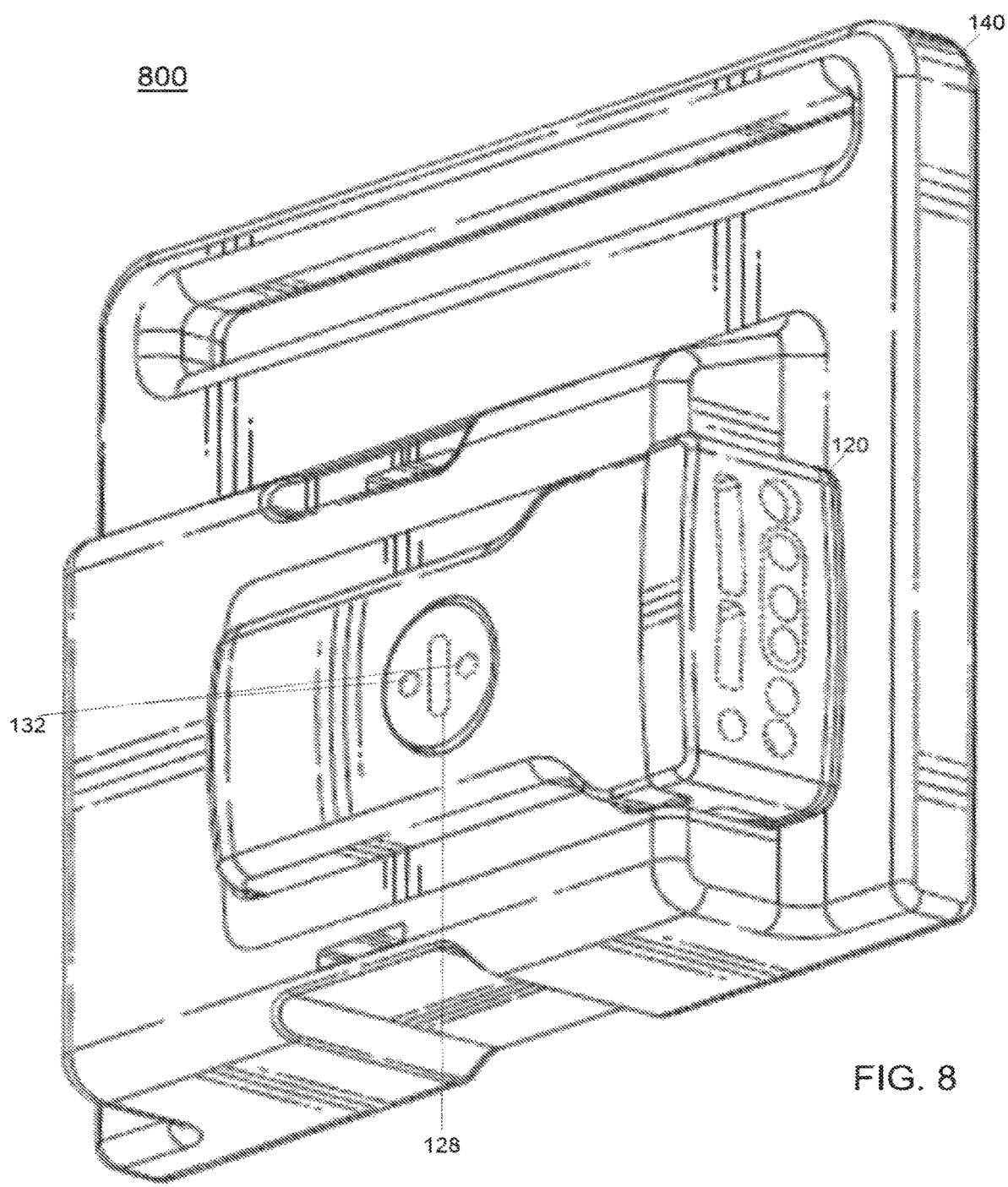
FIG. 8 is a perspective view of the first monitor and the second monitor separate and removed from the monitor mount.
Figure 9:
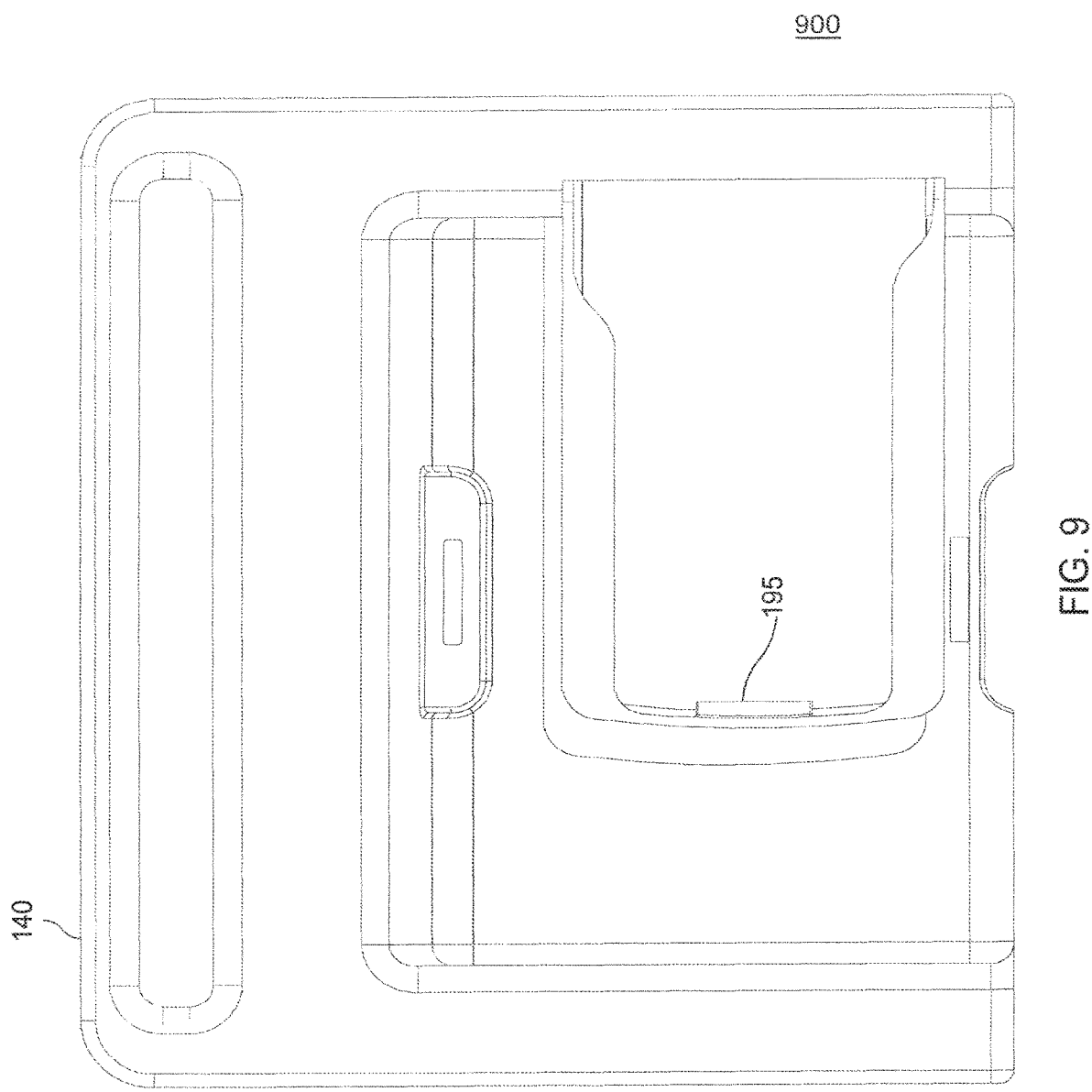
FIG. 9 is a back view of the second monitor.

FIG. 6 is a perspective view 600 showing the second monitor 140 being detachably secured to the monitor mount 160. In some variations, as is illustrated in view 700 of FIG. 7, the electronic visual display 146 of second monitor 140 can surround/obscure at least a portion of the electronic visual display 126 of the first monitor 120. The first monitor 120 can be removed from the monitor mount 160 independent of the second monitor 140 (for example, with reference to FIG. 7 by being removed transversely from the monitor mount 160). In addition, the monitor mount 160 can be arranged to allow left side and/or right side transverse removal from the monitor mount 160. In still other variations, the second monitor 140 with the first monitor 120 disposed therein can be removed from the monitor mount 160. Stated differently, the combination of the first monitor 120 and the second monitor 140 can together be detached from the monitor mount 160.

In some variations, the second monitor 140 can have a shape and size to completely envelop and secure the first monitor 120. With reference to view 800 of FIG. 8, the first monitor 120 can be secured and interface with the second monitor 140. When the first monitor 120 is secured with the second monitor 140, a connection is made by the first electrical connection 190 with the second electrical connector 195. Second electrical connector 195 of second monitor 140 is illustrated in back view 900 of FIG. 9. Similarly, with reference to side view 1900 of FIG. 19, the alternative first monitor 120 can be secured and interface within the open envelope of the alternative second monitor 140. For example, with such an arrangement, the data that otherwise would have been displayed by the electronic visual display 126 of the first monitor 120 can be displayed by the electronic visual display 146 of the second monitor 140.

Figure 10:
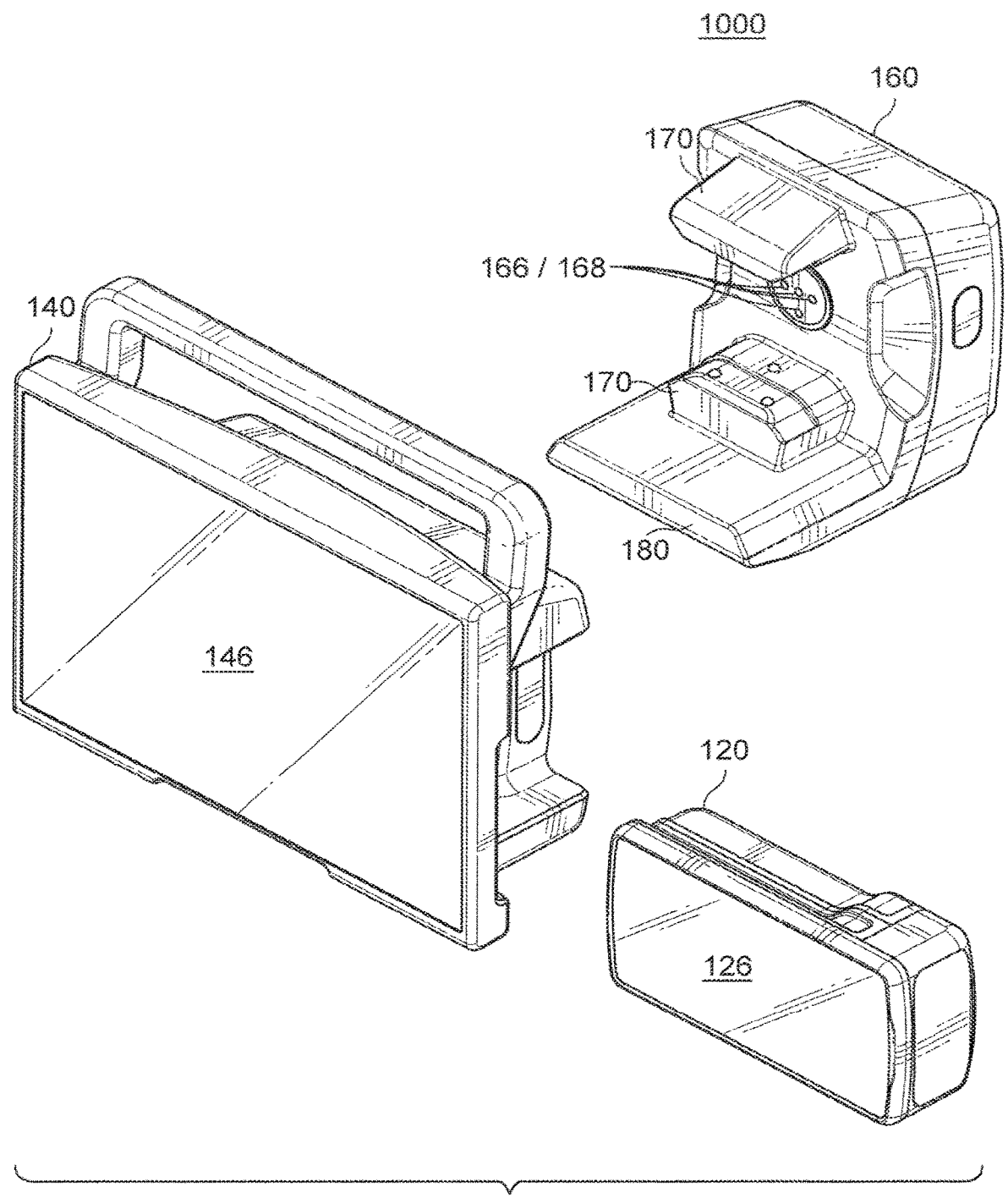
FIG. 10 is an exploded perspective view of another implementation of an alternative first monitor, an alternative second monitor, and an alternative monitor mount.
Figure 11:
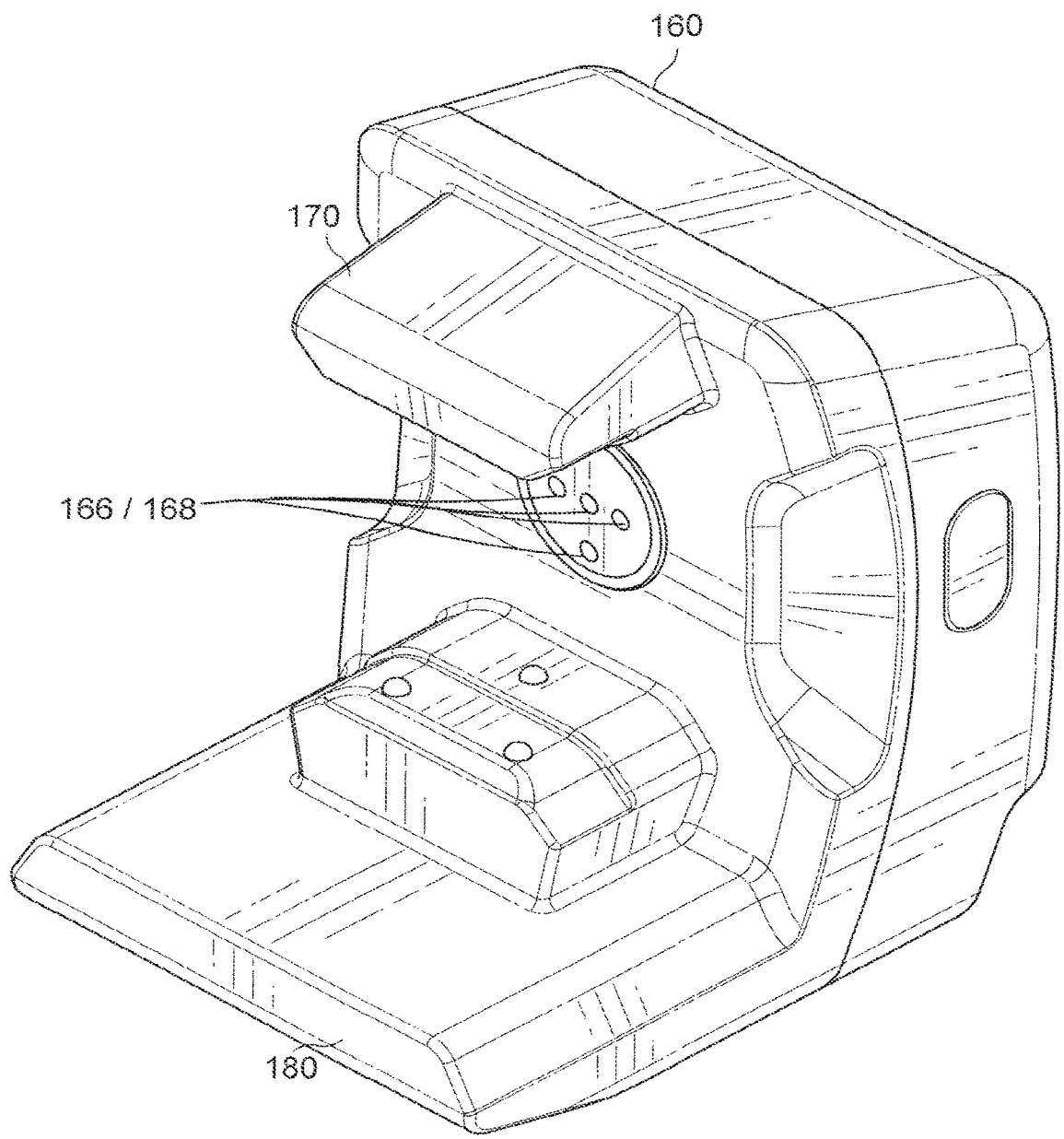
FIG. 11 is a perspective view of the alternative monitor mount.

In some variations, communications interface 166 can be an optical interface providing optical communications between monitor mount 160 and a first monitor 120 and/or between a first monitor 120 and a second monitor 140 coupled together. FIG. 10 is an exploded perspective view 1000 that shows the relationship of an alternative first monitor 120, an alternative second monitor 140, and an alternative monitor mount 160. As shown, the communications interface 166 and the power/source conduit 168 can be placed intermediate the first coupling 170 so that the first monitor 120 may interface therewith. Similarly, the communications interface 166 and the power/source conduit 168 can additionally be placed as part of the second coupling 180 (not shown) so that the second monitor 140 may interface therewith. The perspective view 1100 of FIG. 11 shows additional details in this regard.

Figure 12:
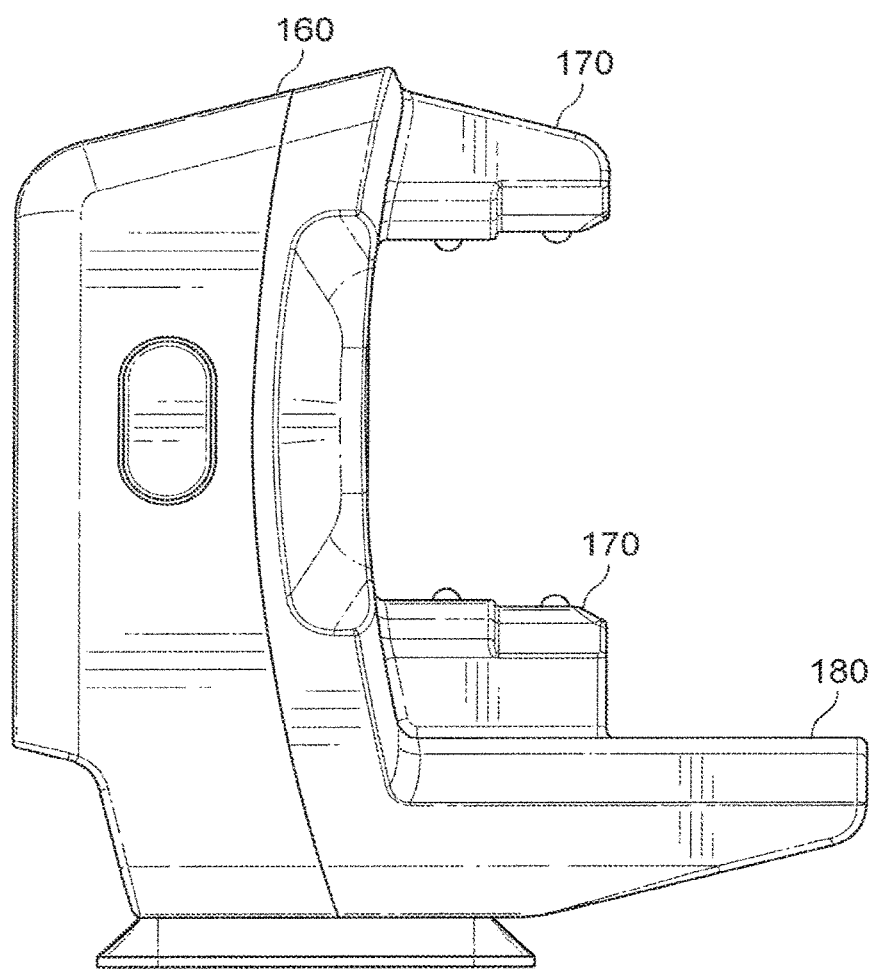
FIG. 12 is a side view of the alternative monitor mount of FIG. 11.

FIG. 12 is a side view 1200 showing various aspects of the alternative monitor mount 160 including detail about how the alternative first monitor 120 can be transversely inserted into the alternative monitor mount 160 (i.e., the alternative first monitor 120 can slide into the alternative monitor mount 160).

Figure 13:
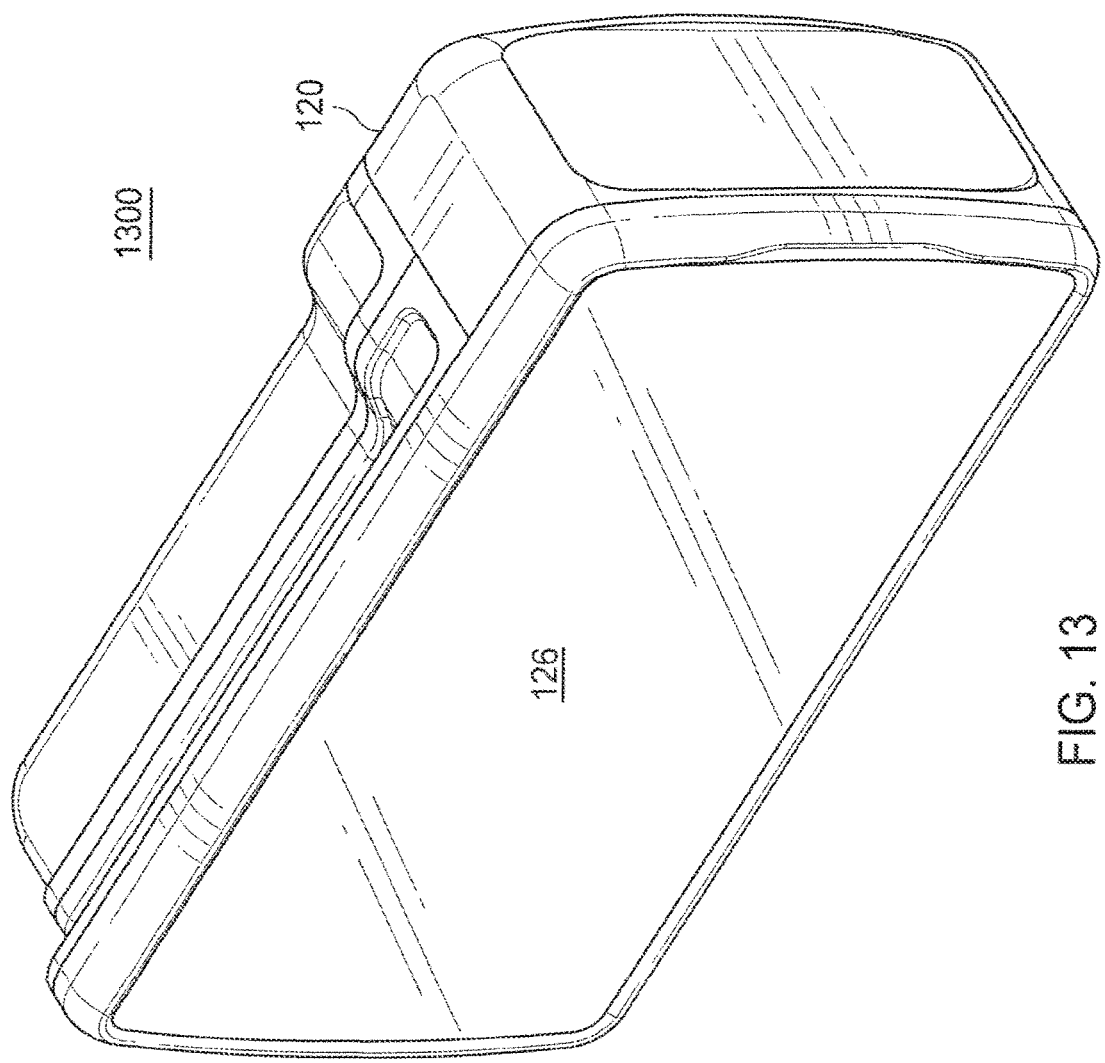
FIG. 13 is a front perspective view of the alternative first monitor.
Figure 14:
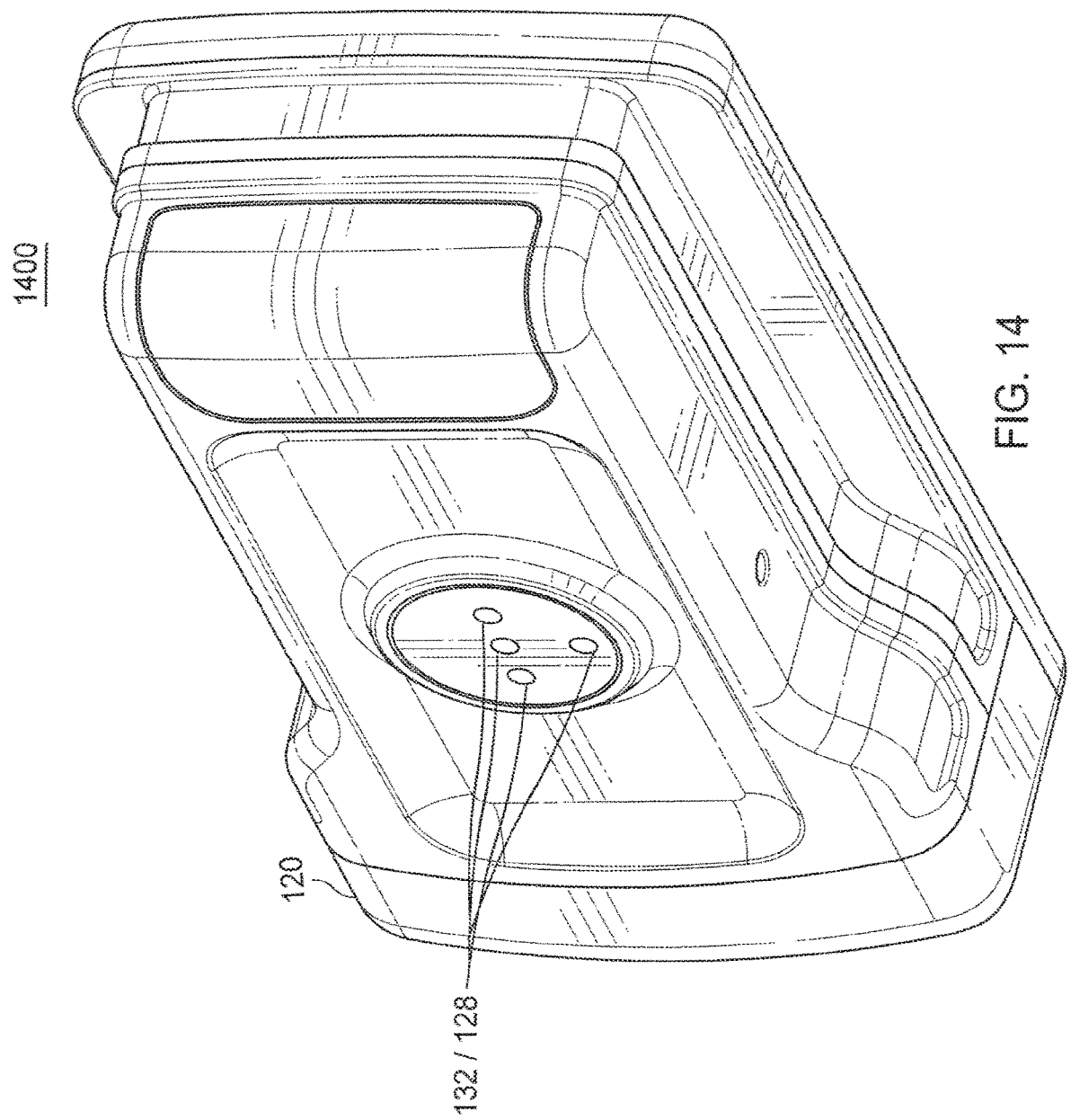
FIG. 14 is a back perspective view of the alternative first monitor of FIG. 13.

FIG. 13 is a front perspective view 1300 of the alternative first monitor 120. As illustrated in FIG. 13, in some variations an alternative first monitor 120 has no first electrical connector 190. Instead, the data communication between the alternative first monitor 120 and alternative second monitor 140 is optical, occurring across communications interface 128 of alternative first monitor 120 as illustrated by the back perspective view 1400 of FIG. 14.

Figure 15:
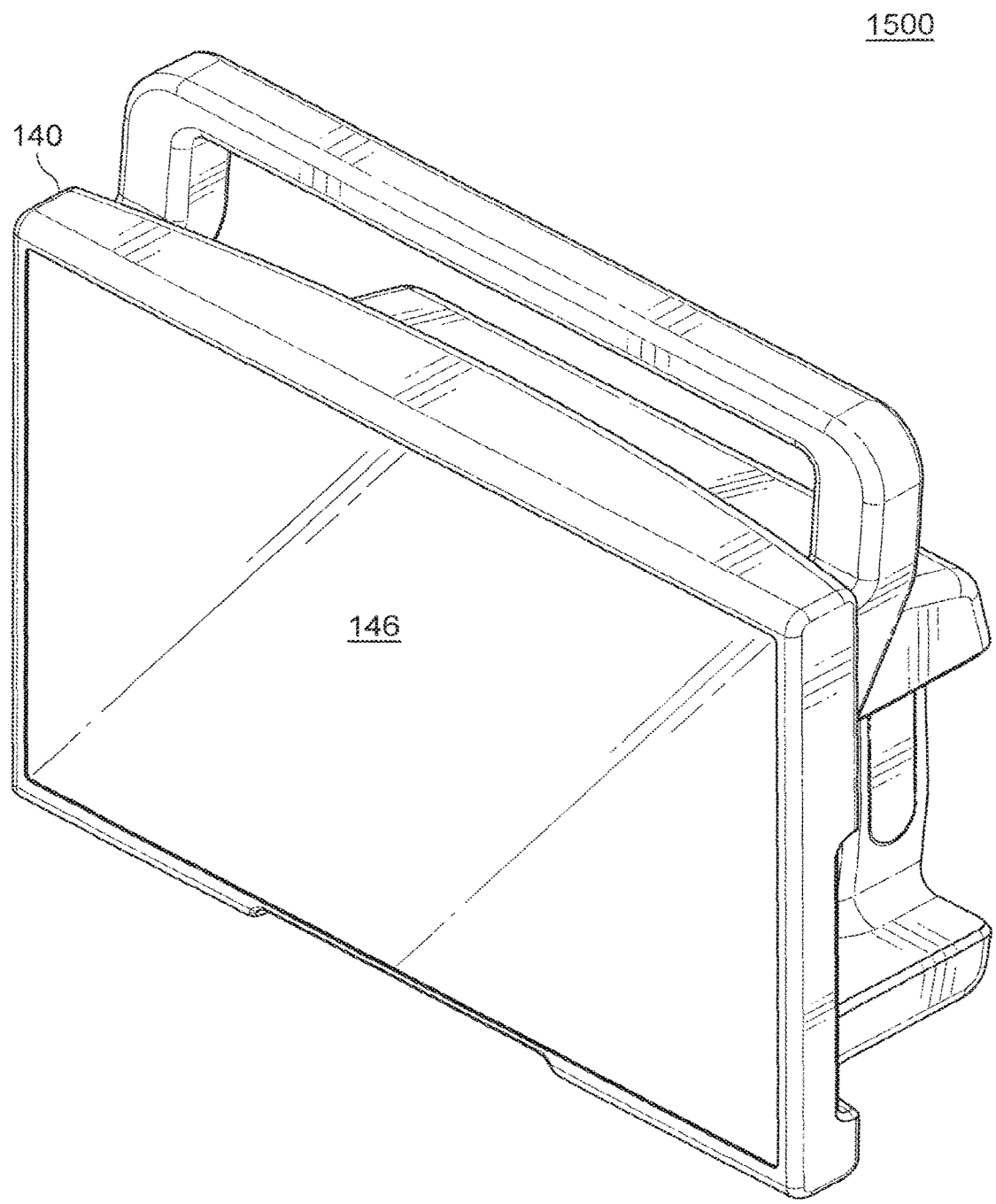
FIG. 15 is a front perspective view of an alternative second monitor.
Figure 16:
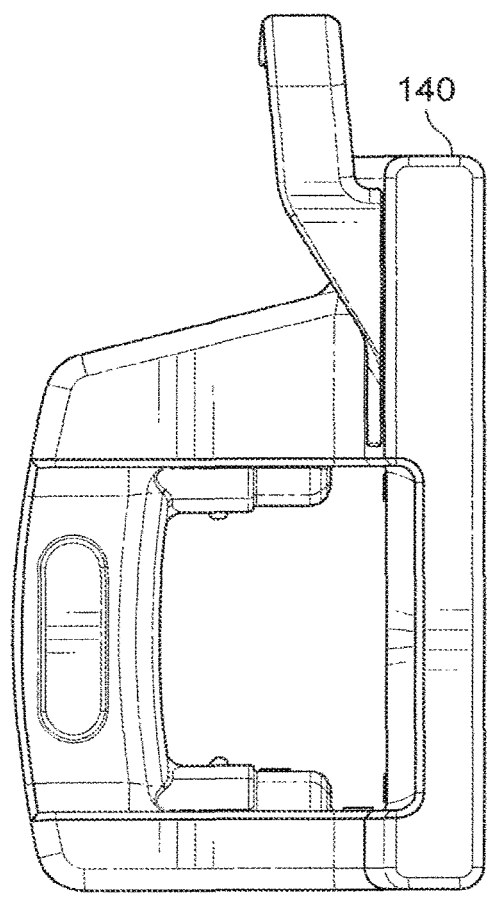
FIG. 16 is a side view of the alternative second monitor of FIG. 15.

FIG. 15 is a front perspective view 1500 of an alternative second monitor 140. FIG. 16 is a side view 1600 of the alternative second monitor 140 of FIG. 16.

Figure 17:
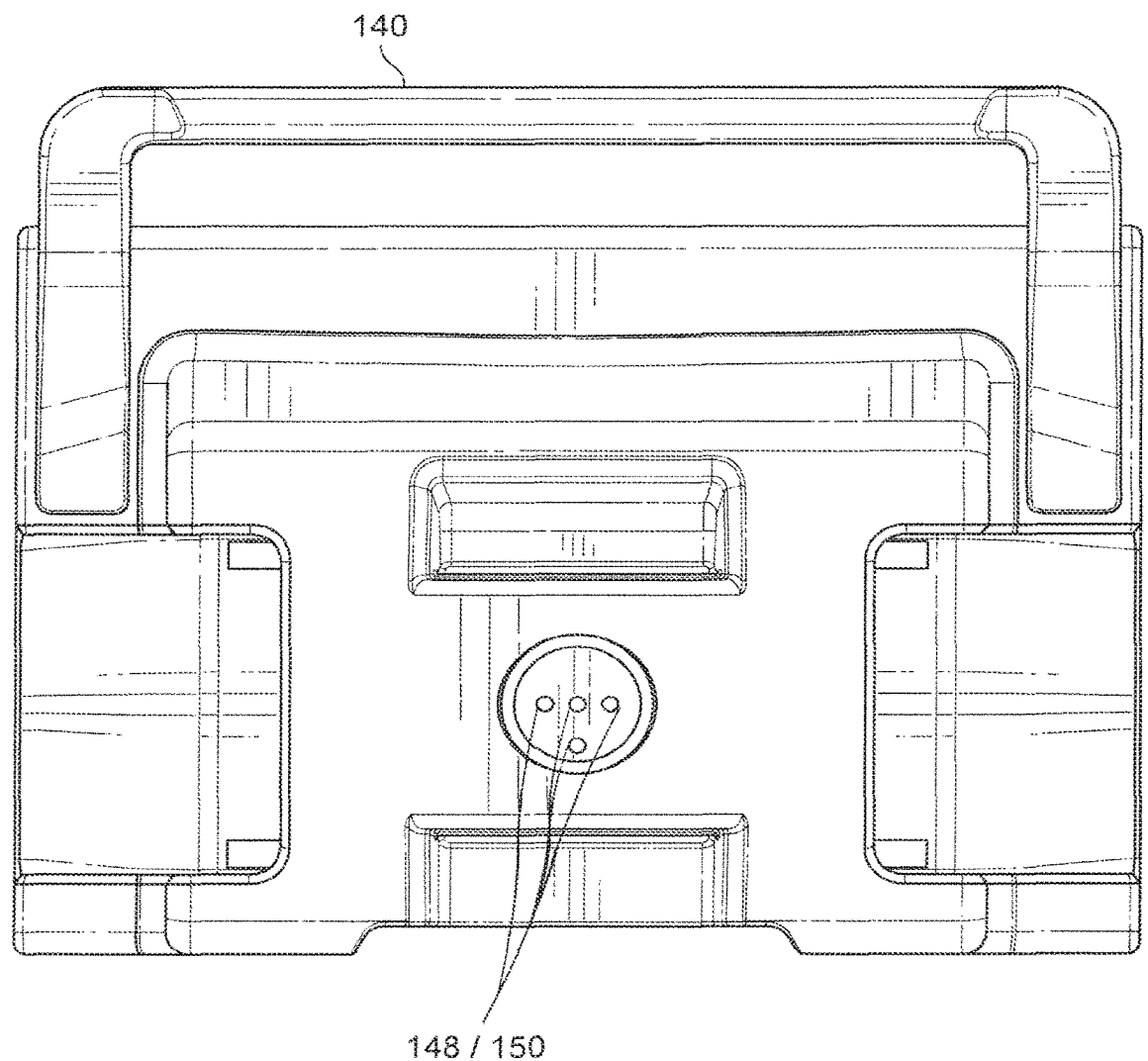
FIG. 17 is a back view of the alternative second monitor of FIG. 15.

FIG. 17 is a back view 1700 of the alternative second monitor of FIG. 15. Data communication between the alternative second monitor 140 and monitor mount 160 can also use an optical communications interface (e.g., communications interface 148).

Figure 18:
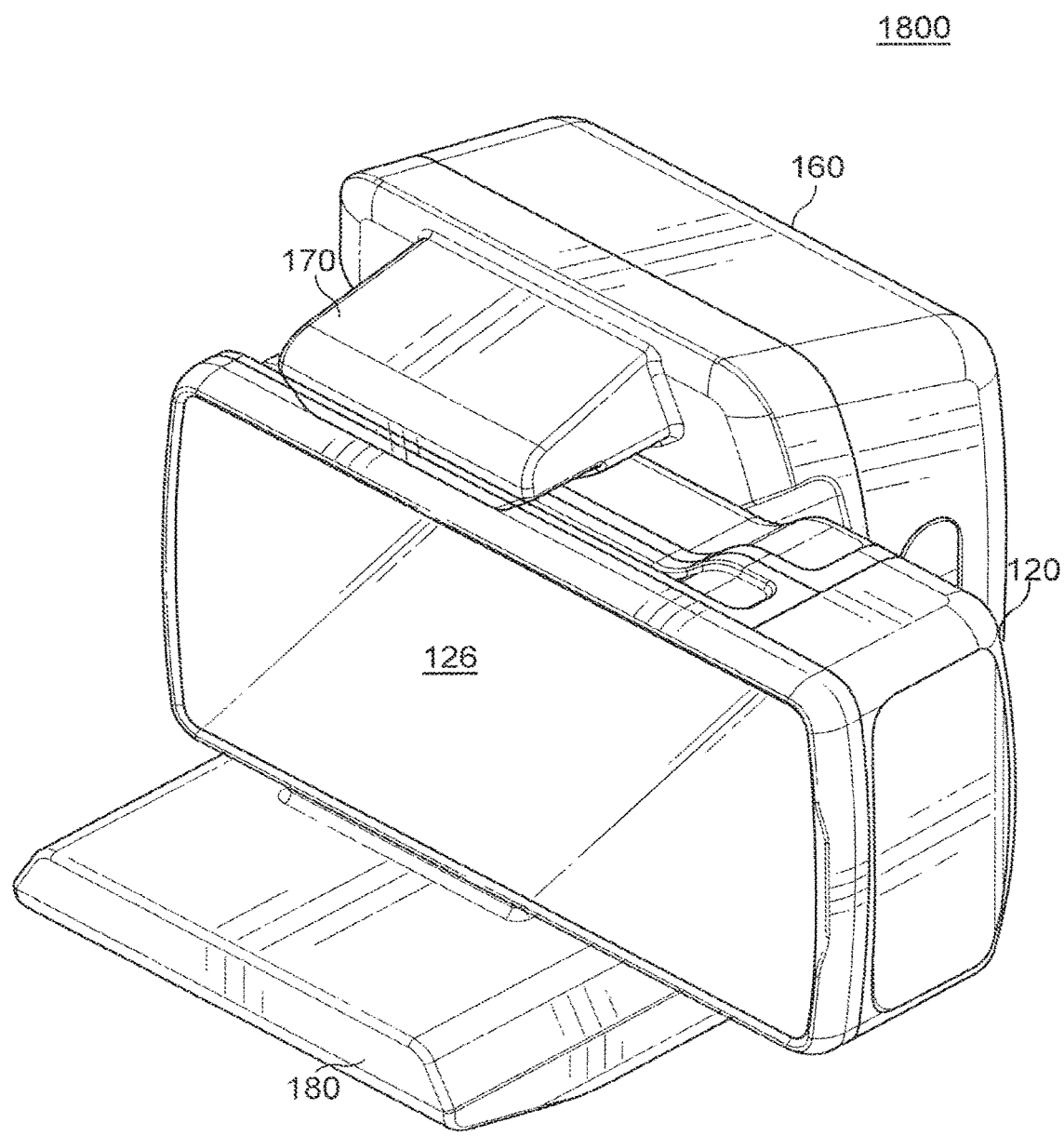
FIG. 18 is a perspective view of the alternative monitor mount detachably securing the alternative first monitor.

FIG. 18 is a perspective view 1600 showing the alternative first monitor 120 being detachably secured to the alternative monitor mount 160.

Figure 19:
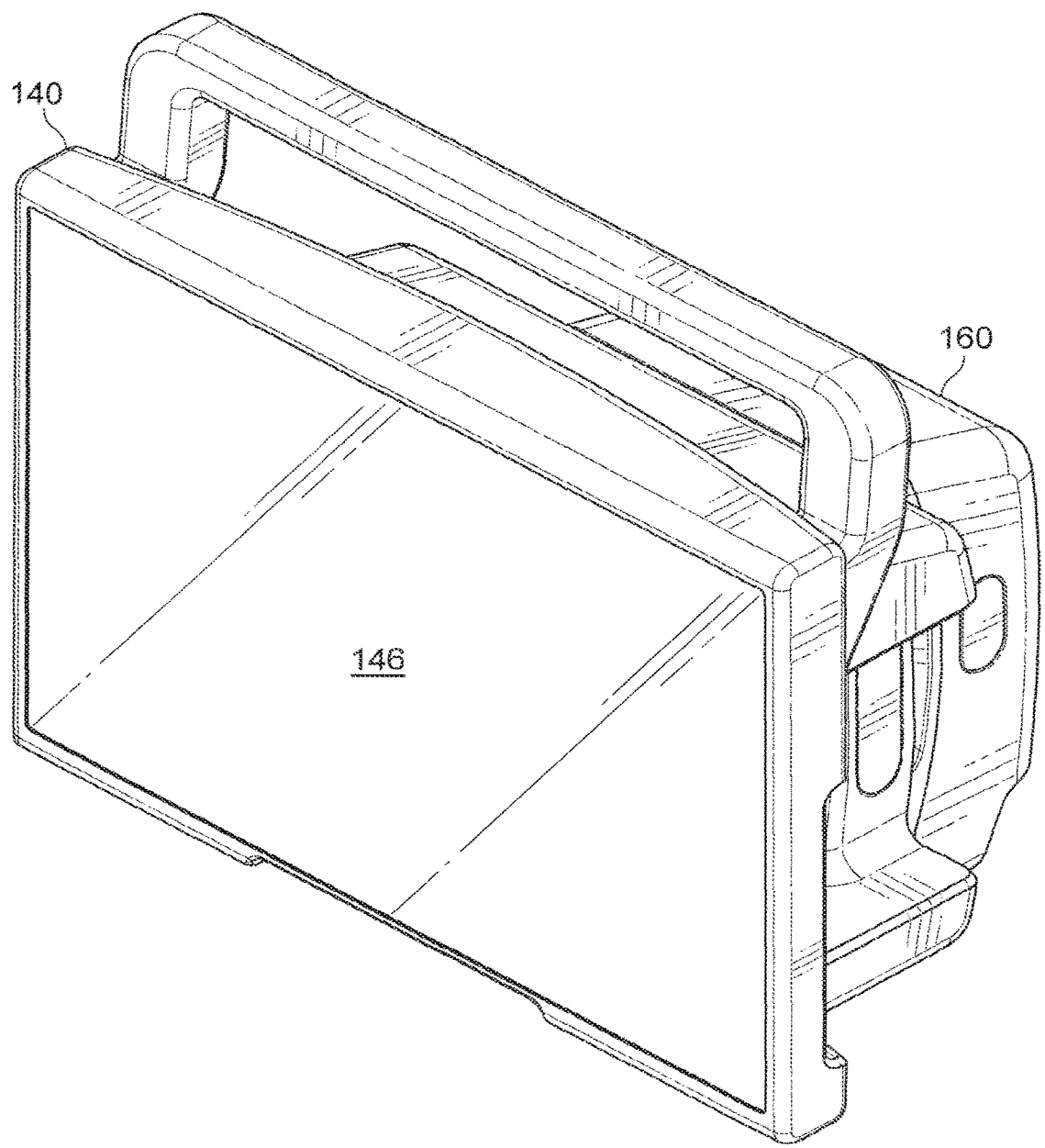
FIG. 19 is a perspective view of the alternative monitor mount detachably securing the alternative second monitor.
Figure 20:
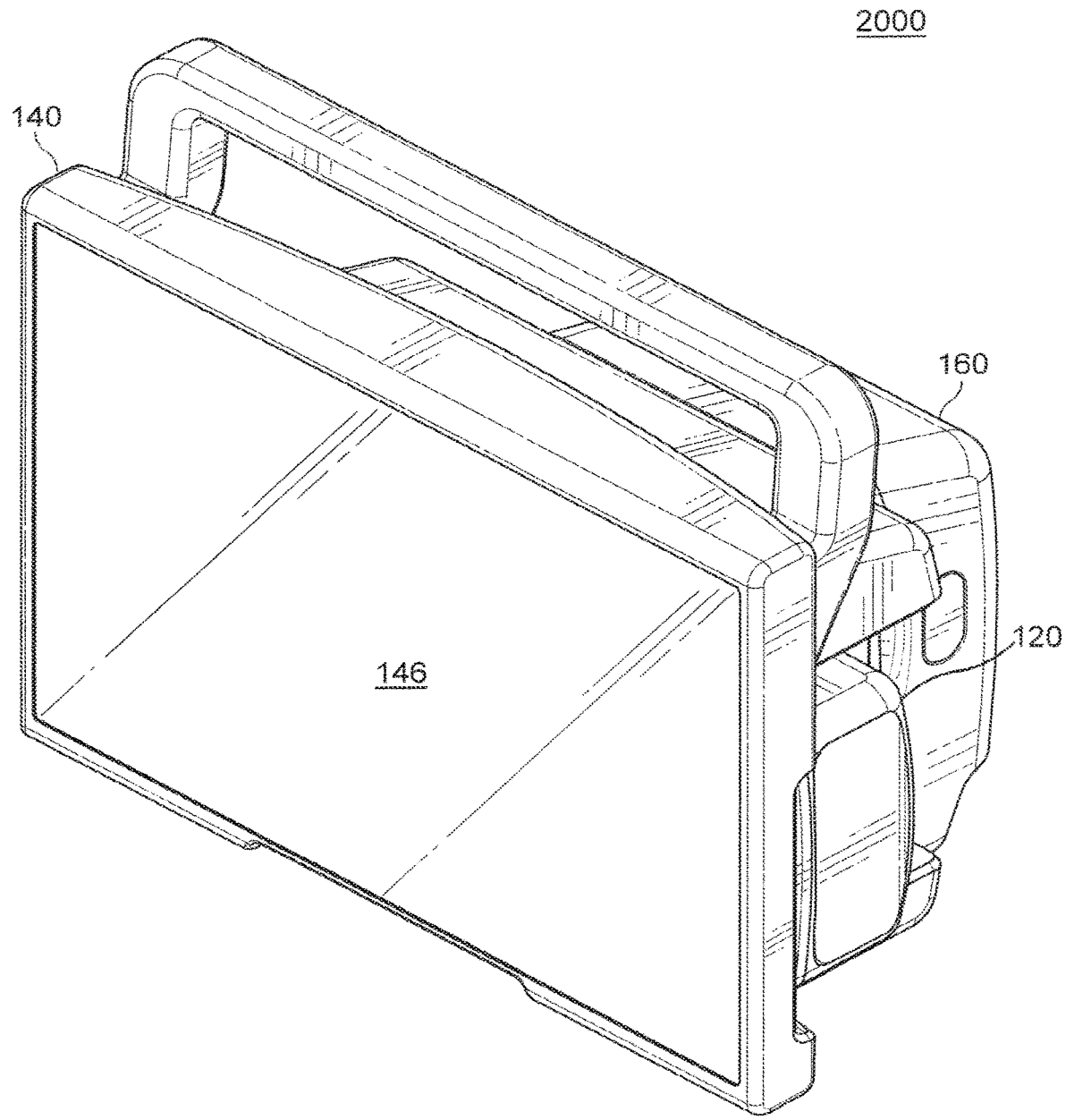
FIG. 20 is a perspective view of the alternative monitor mount detachably securing both the alternative first monitor and the alternative second monitor.

FIG. 19 is a perspective view 1900 showing the alternative second monitor 140 being detachably secured to the alternative monitor mount 160. In some variations, as is illustrated in view 2000 of FIG. 20, the electronic visual display 146 of alternative second monitor 140 can surround/obscure at least a portion of the electronic visual display 126 of the alternative first monitor 120. The alternative first monitor 120 can be removed from the alternative monitor mount 160 independent of the alternative second monitor 140 (for example, with reference to FIG. 19 by being removed transversely from the alternative monitor mount 160). In addition, the alternative monitor mount 160 can be arranged to allow left side and/or right side transverse removal from the alternative monitor mount 160. In still other variations, the alternative second monitor 140 with the alternative first monitor 120 disposed therein can be removed from the alternative monitor mount 160. Stated differently, the combination of the alternative first monitor 120 and the alternative second monitor 140 can together be detached from the alternative monitor mount 160.

In some variations, when the alternative first monitor 120 is mounted within the cavity of the alternative second monitor 140, the communications interface 128 (e.g., optical communications interface), and optionally the power interface 132, on the first monitor 120 provide data communications with, and optionally power to, the alternative second monitor 140 via the communications interface 148 (e.g., optical communications interface), and optionally the power source/conduit 150, on the alternative second monitor 140 within the cavity.

FIG. 21 is a front perspective view 2100 of another alternative first monitor 120 having a handle 121. Handle 121 can facilitate the transverse insertion and/or removal of the alternative first monitor 120 into the cavity of the alternative second monitor 140 and/or into the first coupling 170 of the alternative monitor mount 160. FIG. 22 is a back perspective view 2200 of the alternative first monitor 120 of FIG. 21.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system can include clients and servers. A client and server are generally remote from each other and typically interact through a communication network. The relationship of client and server arises by virtue of computer programs running on the respective computers and having a client-server relationship to each other. The computing systems/devices can include a variety of devices including personal computers, mobile phones, tablet computers, and Internet-of-Things (IoT) devices.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "computer-readable medium" refers to any computer program product, apparatus and/or device, such as for example magnetic discs, optical disks, solid-state storage devices, memory, and Programmable Logic Devices (PLDs), used to provide machine instructions and/or data to a programmable data processor, including a computer-readable medium that receives machine instructions as a computer-readable signal. The term "computer-readable signal" refers to any signal used to provide machine instructions and/or data to a programmable data processor. The computer-readable medium can store such machine instructions non-transitorily, such as for example as would a non-transient solid-state memory or a magnetic hard drive or any equivalent storage medium. The computer-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device (e.g., a CRT (cathode ray tube) or LCD (liquid crystal display) monitor) for displaying information to the user and a keyboard and a pointing device (e.g., a mouse or a trackball) and/or a touch-screen by which the user can provide input to the computer. Other kinds of devices can be used to provide for interaction with a user as well; for example, feedback provided to the user can be any form of sensory feedback (e.g., visual feedback, auditory feedback, and/or tactile feedback); and input from the user can be received in any form, including acoustic, speech, or tactile input.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system, comprising:
    a monitor mount;
    a first monitor detachably securable to the monitor mount and defining a first forward surface and a first side surface, the first monitor including:
        a first visual display on the first forward surface, and
        a data-collecting sensor interface on the first side surface;
    a second monitor detachably securable to the monitor mount such that, when assembled with the first monitor and the monitor mount, the first monitor is positioned between the second monitor and the monitor mount, the second monitor defining a second forward surface and including a second visual display on the second forward surface.

2. The system of claim 1, wherein the first monitor collects and displays data as an independent device when detached from the second monitor and from the monitor mount.

3. The system of claim 1, wherein, when the first monitor, the second monitor, and the monitor mount are assembled, the first visual display is obscured and the second visual display second monitor displays data collected by the first monitor.

4. The system of claim 1, wherein the first monitor and the monitor mount, secured by a first coupling, collect and display data as an independent subsystem with the second monitor detached.

5. The system of claim 1, wherein a first coupling between the first monitor and the monitor mount has symmetric features to detachably secure the first monitor in a first orientation or in a second orientation, the second orientation being rotated 180 degrees in a plane of the first forward surface compared to the first orientation.

6. The system of claim 1, wherein the first monitor includes a handle on the first side surface near the sensor interface, the handle being angled to facilitate user access to the sensor interface and enable the user to secure or detach the first coupling.

7. The system of claim 1, wherein:
    a first coupling is secured by a process that includes placing a back portion of the first monitor against a forward portion of the monitor mount, and
    the first coupling is detached by a process that includes removing the back portion of the first monitor from the forward portion of the monitor mount.

8. The system of claim 1, wherein a first coupling is secured or detached by a process that includes sliding a back portion of the first monitor laterally along a forward portion of the monitor mount.

9. The system of claim 1, wherein at least one of a first coupling between the first monitor and the monitor mount and a second coupling between the second monitor and the monitor mount comprises a power bus.

10. The system of claim 1, wherein at least one of a first coupling between the first monitor and the monitor mount and a second coupling between the second monitor and the monitor mount comprises an optical, electrical, magnetic, or electromagnetic connection.

11. The system of claim 1, further comprising a coupling between the first monitor and the second monitor,
    the first monitor and the second monitor being operable to collect and display data as a subsystem independent of the monitor mount when the coupling is secured and the first monitor and the second monitor are detached from the monitor mount; and
    the coupling enabling the data collected by the first monitor to be displayed by the second monitor.

12. The system of claim 11, wherein:
    the second monitor defines a cavity;
    a first mating portion of the coupling is on a second side of the first monitor, the second side opposing the first side;
    a second mating portion of the coupling is at an end of the cavity; and
    the coupling is secured by sliding the first monitor into the cavity.

13. The system of claim 11, wherein the coupling comprises a power bus.

14. The system of claim 11, wherein the coupling comprises an optical, electrical, magnetic, or electromagnetic connection.

15. A method, comprising:
    positioning a sensor to monitor a medical parameter of a patient,
    connecting the sensor to a sensor interface of a first monitor,
    collecting data from the sensor and displaying it on a first visual display of the first monitor;
    co-locating the patient, the first monitor, and a subsystem, wherein:
        the subsystem comprises a second monitor;
        the coupling detachably secures the first monitor to the second monitor such that the second monitor obscures the first visual display of the first monitor; and
    the data collected from the sensor is displayed on a second visual display of the second monitor;
    magnetically or electromagnetically coupling the first monitor to the subsystem while the sensor remains connected to the sensor interface and positioned relative to the patient; and
    continuously collecting and displaying uninterrupted data from the patient during the co-locating and the coupling.

16. The method of claim 15, wherein:
    the subsystem comprises a monitor mount,
    the coupling detachably secures the first monitor to the monitor mount, and
    the data collected from the sensor continues to be displayed on the first visual display of the first monitor.

17. The method of claim 16, wherein:
the coupling positions the first monitor between the monitor mount and the second monitor.

18. The method of claim 15, wherein the first monitor is coupled to the subsystem in one of at least two alternative orientations.

19. The method of claim 15, wherein the subsystem provides electrical power to the first monitor.

20. The method of claim 15, wherein the subsystem comprises additional sensors.

21. The method of claim 15, wherein the coupling to the subsystem expands the processing power or the network connectivity available to the first monitor.

22. A non-transitory computer-readable storage medium containing instructions that, when executed, cause a processor in a first monitor to:

collect data from a sensor through a sensor interface;
determine whether a second monitor is magnetically or electromagnetically coupled to the first monitor such that the second monitor obscures a first visual display of the first monitor;
if so, bypass the first visual display of the first monitor and display the data on a second visual display of the second monitor.

23. The non-transitory computer-readable storage medium of claim 22, further comprising instructions to:

determine whether a monitor mount is connected to the first monitor;
if so, utilize any power bus, network interface, or processor available through the connection to the monitor mount.

* * * * *